US008880352B2

(12) United States Patent
Kale et al.

(10) Patent No.: US 8,880,352 B2
(45) Date of Patent: Nov. 4, 2014

(54) SYSTEM AND METHOD FOR ANALYZING AN ELECTROPHYSIOLOGICAL SIGNAL

(75) Inventors: Amit Kale, Karnataka (IN); Stefan Kimmer, Dresden (DE); Kaustubh Kulkarni, Karnataka (IN)

(73) Assignee: Siemens Aktiengesellschaft, Munich (DE)

(*) Notice: Subject to any disclaimer, the term of this patent is extended or adjusted under 35 U.S.C. 154(b) by 1011 days.

(21) Appl. No.: 12/955,092

(22) Filed: Nov. 29, 2010

(65) Prior Publication Data

US 2012/0136580 A1    May 31, 2012

(51) Int. Cl.
G06F 19/00     (2011.01)
A61B 5/0452    (2006.01)
A61B 5/00      (2006.01)

(52) U.S. Cl.
CPC .......... *A61B 5/04525* (2013.01); *A61B 5/7267* (2013.01)
USPC ............. 702/19; 600/526; 382/128; 128/898

(58) Field of Classification Search
CPC ...... A61B 5/029; A61B 8/065; A61B 5/7285; A61B 5/0051; A61B 5/6814; A61B 5/031; A61B 5/7267; A61B 5/04525
USPC ............ 702/19; 600/483, 485, 425, 526, 454, 600/336, 509, 508; 382/128; 128/898
See application file for complete search history.

(56) References Cited

U.S. PATENT DOCUMENTS

| | | | |
|---|---|---|---|
| 5,311,873 A * | 5/1994 | Savard et al. ................. | 600/508 |
| 7,398,208 B2 | 7/2008 | Kaemmerer | |
| 7,471,816 B2 * | 12/2008 | Palmer .......................... | 382/128 |
| 8,483,808 B2 * | 7/2013 | Dong et al. .................... | 600/509 |
| 8,588,925 B2 * | 11/2013 | Carbunaru et al. ............. | 607/60 |
| 8,626,277 B2 * | 1/2014 | Felix et al. .................... | 600/513 |
| 2004/0249639 A1 | 12/2004 | Kaemmerer | |
| 2006/0235315 A1 * | 10/2006 | Akselrod et al. .............. | 600/509 |
| 2007/0014459 A1 * | 1/2007 | Palmer .......................... | 382/128 |
| 2008/0051668 A1 * | 2/2008 | Bardy ........................... | 600/483 |
| 2010/0185084 A1 * | 7/2010 | Zhang ........................... | 600/425 |
| 2011/0077541 A1 * | 3/2011 | Dong et al. .................... | 600/515 |
| 2013/0223709 A1 * | 8/2013 | Wagner ......................... | 382/128 |

OTHER PUBLICATIONS

Martinez, J.P.; Almeida, R.; Olmos, S.; Rocha, A.P.; Laguna, P.; , "A wavelet-based ECG delineator: evaluation on standard databases," Biomedical Engineering, IEEE Transactions on , vol. 51, No. 4, pp. 570-581, Apr. 2004.

(Continued)

*Primary Examiner* — Carol S Tsai

(74) *Attorney, Agent, or Firm* — Brennan K Bradley

(57) ABSTRACT

A system and a method of analyzing an electrophysiological signal, wherein the system comprises an acquisition device for acquiring a test electrophysiological signal associated with an anatomical part of a patient and a processor configured to divide a cycle of the test electrophysiological signal into test time windows, compare a test signal value of each of the test time windows with a reference signal value of reference time windows of the reference segments of respective representations representing respective predetermined morphological classes to obtain a difference, define grid points associated with respective test time windows, respective reference time windows and respective differences, obtain a warping path using the grid points non-linearly in a predetermined order, sum differences along the grid points of each of the warping paths to obtain a cumulative distance for each of the warping paths, and classify the test electrophysiological signal into one of the respective predetermined morphological classes corresponding to the warping path of the respective representation having the least cumulative distance.

20 Claims, 16 Drawing Sheets

(56) References Cited

OTHER PUBLICATIONS

Cherla, S.; Kulkarni, K.; Kale, A.; Ramasubramanian, V.; , "Towards fast, view-invariant human action recognition," Computer Vision and Pattern Recognition Workshops, 2008. CVPRW '08. IEEE Computer Society Conference on , vol., no., pp. 1-8, Jun. 23-28, 2008.

Andreao, R.V.; Dorizzi, B.; Boudy, J.; , "ECG signal analysis through hidden Markov models," Biomedical Engineering, IEEE Transactions on , vol. 53, No. 8, pp. 1541-1549, Aug. 2006.

Cuiwei Li; Chongxun Zheng; Changfeng Tai; , "Detection of ECG characteristic points using wavelet transforms," Biomedical Engineering, IEEE Transactions on , vol. 42, No. 1, pp. 21-28, Jan. 1995.

Nicholas P. Hughes, et al., "Markov Models for Automated ECG Interval Analysis", Department of Engineering Science, University of Oxford 2008.

Kaustubh Kulkarni et al., "A Framework for Indexing Human Actions in Video", 1st International Workshop on Machine Learning for Vision-Based Motion Analysis at ECCF 2008, Marseille, France, Oct. 2008.

Julien Thomas; Cedric Rose; Francois Charpillet; , "A Multi-HMM Approach to ECG Segmentation," Tools with Artificial Intelligence, 2006. ICTAI '06. 18th IEEE International Conference on , vol., no., pp. 609-616, Nov. 2006.

Hermann Ney; "The Use of a One-Stage Dynamic Programming Algorithm for Connected Word Recognition", IEEE Transactions on Acoustic, Speech, and Signal Proceeding, vol. ASSP-32, No. 2, pp. 263-271, Apr. 1984.

Rodrigo Varejao Andreao and Jerome Boudy; "Combining Wavelet Transform and Hidden Markov Models for ECG Segmentation", Research Article, Hindawi Publishing Corporation, EURASIP Journal on Advances in Signal Processing, vol. 2007, Article ID 56215, 8 pages 2007.

H.J.L.M. Vullings, M.H.G. Verhaegen, H.B. Verbruggen; "Automated ECG Segmentation with Dynamic Time Warping", Proceedings of the 20th Annual International Conference of the IEEE Engineering in Medicine and Biology Society, vol. 20, No. 1, pp. 163-166, 1998.

Zelinski, R.; Class, F.; , "A learning procedure for speaker-dependent word recognition systems based on sequential processing of input tokens," Acoustics, Speech, and Signal Processing, IEEE International Conference on ICASSP '83. , vol. 8, no., pp. 1053- 1056, Apr 1983.

* cited by examiner

TEST TIME WINDOWS
T(ms)

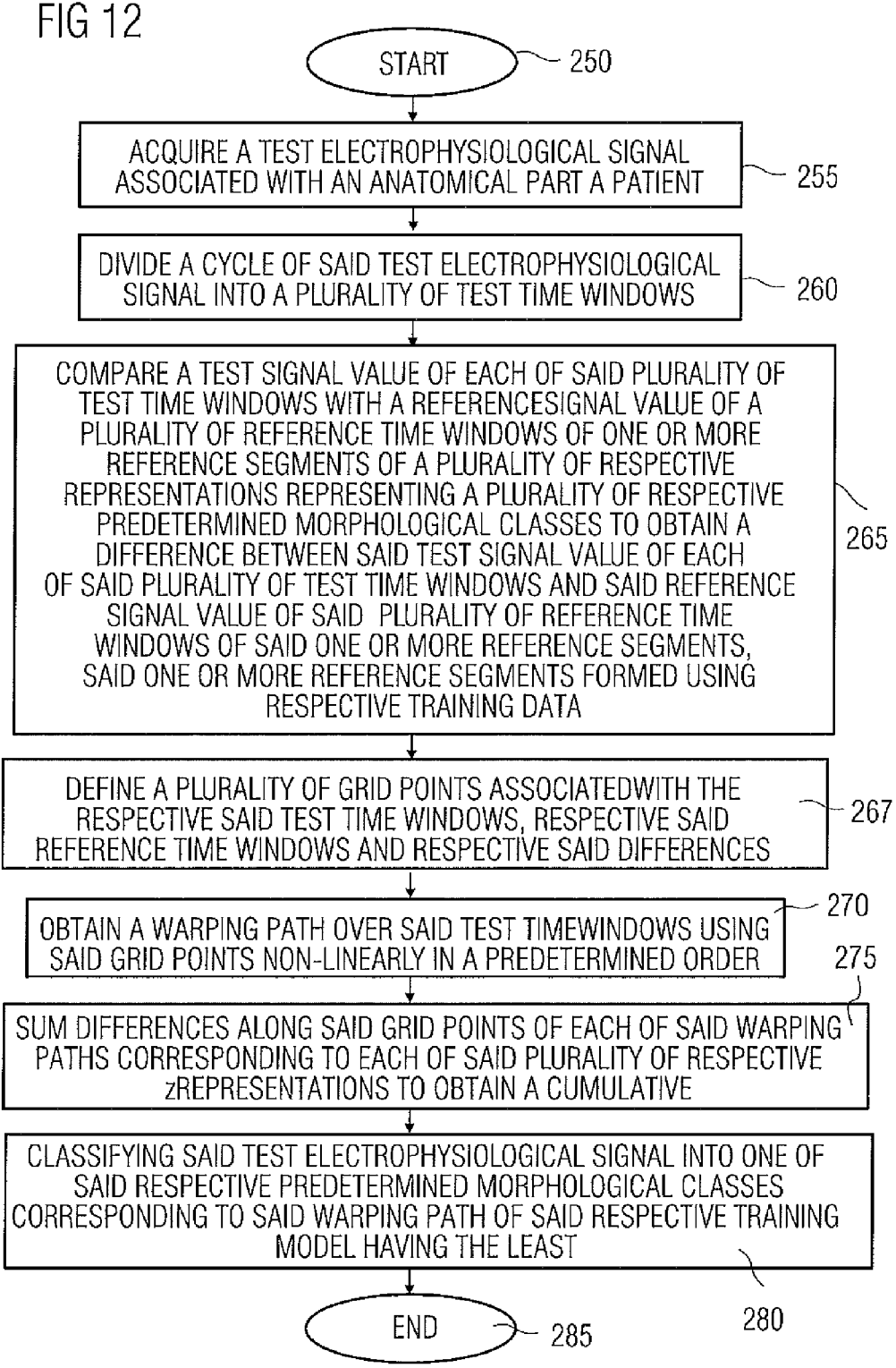

SYSTEM AND METHOD FOR ANALYZING AN ELECTROPHYSIOLOGICAL SIGNAL

FIELD OF INVENTION

The present invention relates to a system and method for analyzing an electrophysiological signal, in particular, for classifying and segmenting the electrophysiological signal.

BACKGROUND OF INVENTION

An electrophysiological signal represents an electrical activity of a part of a body of a patient. For example, it can include electrical activities of a heart or neurons and the like. Thus, the electrophysiological signals are used for diagnosis of abnormalities of the part of the body the signal is associated with. Diagnosis of abnormalities using electrophysiological signals requires classification and segmentation of the electrophysiological signals. Classification of the electrophysiological signal into a morphological class is an important clinical parameter in identifying the type of abnormality. Segmentation of the electrophysiological signal provides the points of onset and offset of portions of the electrophysiological signal which correlate with the electrical activity of the body part.

SUMMARY OF THE INVENTION

In view of the foregoing, an embodiment herein includes a system for analyzing an electrophysiological signal comprising a system for analyzing an electrophysiological signal, comprising an acquisition device for acquiring a test electrophysiological signal associated with an anatomical part of a patient, and a processor configured to divide a cycle of the test electrophysiological signal into test time windows, compare a test signal value of each of the test time windows with a reference signal value of the reference time windows of one or more reference segments of the respective representations representing respective predetermined morphological classes to obtain a difference between the test signal value of each of the test time windows and the reference signal value of the reference time windows of the one or more reference segments, the one or more reference segments being formed using respective training data, define grid points associated with respective test time windows, respective reference time windows and respective differences, obtain a warping path over test time windows using the grid points non-linearly in a predetermined order, sum differences along the grid points of each of the warping paths corresponding to each of the respective representations to obtain a cumulative distance for each of the warping paths, and classify the test electrophysiological signal into one of the respective predetermined morphological classes corresponding to the warping path of the respective representation having the least cumulative distance.

Another embodiment includes, a system for analyzing an electrophysiological signal, comprising, an acquisition device for acquiring a test electrophysiological signal associated with an anatomical part of a patient, a memory device having stored therein respective representations representing respective predetermined morphological classes, each of the respective representations formed using one or more reference segments, each of the one or more reference segments being formed using respective training data, each of the reference segments comprising reference time windows and a processor configured to divide a cycle of the test electrophysiological signal into test time windows, compare a test signal value of each of the test time windows with a reference signal value of the reference time windows of the one or more reference segments to obtain a difference between the test signal value of each of the test time windows and the reference signal value of the plurality of reference time windows of the one or more reference segments, define grid points associated with the respective test time windows, respective reference time windows and respective differences, obtain a warping path over test time windows using grid points non-linearly in a predetermined order, sum differences along the grid points of each of the warping paths corresponding to each of the respective representations to obtain a cumulative distance for each of the warping paths, and classify the test electrophysiological signal into one of the respective predetermined morphological classes corresponding to the warping path of the respective representation having the least cumulative distance.

In accordance with another aspect of the invention, a method of analyzing an electrophysiological signal is provided, wherein the method comprises, acquiring a test electrophysiological signal associated with an anatomical part of a patient, dividing a cycle of the test electrophysiological signal into test time windows, comparing a test signal value of each of the test time windows with a reference signal value of reference time windows of one or more reference segments of respective representations representing respective predetermined morphological classes to obtain a difference between the test signal value of each of the test time windows and the reference signal value of the reference time windows of the one or more reference segments, the one or more reference segments being formed using respective training data defining grid points associated with the respective test time windows, respective reference time windows and respective differences, obtaining a warping path over the test time windows using the grid points non-linearly in a predetermined order, summing differences along the grid points of each of the warping paths corresponding to each of the respective representations to obtain a cumulative distance for each of the warping paths, and classifying the test electrophysiological signal into one of the respective predetermined morphological classes corresponding to the warping path of the respective training model having the least cumulative distance.

BRIEF DESCRIPTION OF THE DRAWINGS

The present invention is further described hereinafter with reference to exemplary embodiments shown in the accompanying drawings, in which:

FIG. 12 illustrates a flow chart of a process used by a system for analyzing an electrophysiological signal according to an embodiment herein.

DETAILED DESCRIPTION OF INVENTION

Figure 1:
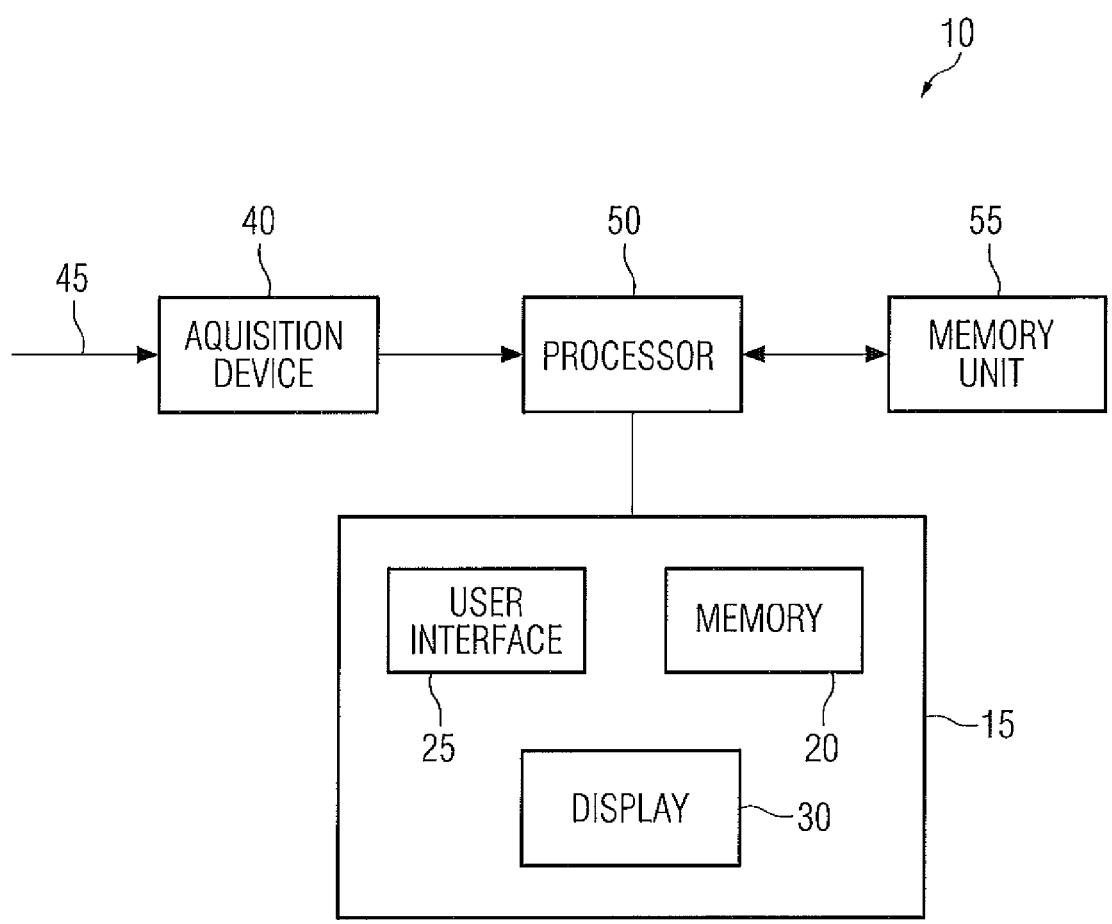
FIG. 1 illustrates a block diagram of a system for analyzing an electrophysiological signal according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Embodiments described herein provide a robust solution for automated classification and segmentation of an electrophysiological signal. The segmentation and classification of the electrophysiological signal is performed by non-linearly comparing the electrophysiological signal with representations formed using training data in a predetermined order.

In the context of the discussion herein, certain terms have been defined/explained as mentioned below:

The term "predetermined morphological classes" or "morphological classes" as used in the context of the illustrated embodiments refers to different medical conditions of the anatomical part of the patient which can be determined using the electrophysiological signal representing the anatomical part.

The term "cycle" as used in the context of the illustrated embodiments refers to one period of the electrophysiological signal as electrophysiological signals are periodic in nature.

The term "representation" as used in the context of the illustrated embodiments represents training data corresponding to a morphological class.

The term "distance" in general as used in the context of the illustrated embodiments defines a measure of dissimilarity between two signals.

The term "summing distances along the warping path" as used in the context of the illustrated embodiments refers to accumulating the distances along the warping path. The distances can be accumulated along the pointers of the warping path.

The term "cumulative distance" as used in the context of the illustrated embodiments is the accumulated differences with respect to a sequence of grid points along the warping path.

The term "compare non-linearly" as used in the context of the illustrated embodiment refers to expanding or compressing portions of signals so that the portions are aligned for comparison.

The term "predetermined order" as used in the context of the illustrated embodiment refers to the continuity constraint of the physical nature of the patterns to be compared. The patterns herein refer to the cycle of the test electrophysiological signal and the reference segments of the representations.

The term "warping path" as used in the context of the illustrated embodiment refers to a path obtained by tracking the grid points obtained by comparing the cycle of the test electrophysiological signal with the reference segments of a representation.

The term "reference segment" as used in the context of the illustrated embodiment represents one or more similar portions of the training data corresponding to each of the morphological classes.

The term "characteristic vector" as used in the context of the illustrated embodiment represents a signal value in a particular time instance.

The term "forced aligned onepass dynamic programming algorithm" as used in the context of the illustrated embodiment refers to an onepass dynamic programming algorithm using which transition from one portion to another portion of a signal is performed in a predetermined order.

The term "intersection of warping path with boundary of a reference segment" as used in the context of the illustrated embodiment refers to the point at which the warping path obtained intersects with the boundary of the reference segment of the representation.

The term "time window" as used in the context of the illustrated embodiment refers to a particular time instance of a signal.

The term "test electrophysiological signal" as used in the context of the illustrated embodiment refers to an electrophysiological signal representing electrophysiological activity of an anatomical part of a patient under diagnosis.

FIG. 1 illustrates a block diagram of a system 10 for analyzing an electrophysiological signal according to an embodiment herein. The "electrophysiological signal" used herein includes any signal representing electrical activity of an anatomical part of a patient. The electrophysiological signal is periodic in nature and, includes, but is not limited to, an electrocardiography signal, an intra-cardiac electrocardiography signal, an electroencephalography signal, an electrocorticography signal, an electromyography signal, an electrooculography signal, an electroretinography signal, an electroantennography signal, and an audiology signal. The system 10 includes one or more processing devices (e.g., workstations, computers or portable devices such as notebooks, Personal Digital Assistants, phones) 15 that individually include memory 20, user interface 25 and a display 30. The system 10 also includes an acquisition device 40, a processor 50, and a memory device 55. The display 30 of the processing device 15 can be used for presenting images to a clinician. According to an aspect, a plurality of representations representing a plurality of respective predetermined morphological classes can be stored at the memory device 55. The predetermined morphological classes are the different medical conditions of the anatomical part of the patient which can be determined using the electrophysiological signal representing the anatomical part. For example, the predetermined morphological classes can include, (a) healthy, (b) disease A, (c) disease B, (3) disease C, etc.

The acquisition device 40 acquires a test electrophysiological signal 45 associated with a part of a body of a patient. The test electrophysiological signal 45 is an electrophysiological signal representing electrophysiological activity of an anatomical part of a patient under diagnosis. The test electrophysiological signal 45 may be received directly from electrodes coupled to the patient or may be transmitted remotely from the electrodes via any intermediate means. In certain aspects, the test electrophysiological signal 45 may be detected using optical means and the acquisition device 40 can acquire the detected test electrophysiological signal 45 from the optical detectors. The acquisition device 40 pre-processes the test electrophysiological signal to detect a single cycle of the test electrophysiological signal 45. The single cycle of the test electrophysiological signal 45 detected is provided to the processor 50. On receiving the cycle of the test electrophysiological signal 45, the processor 50 is configured to divide the cycle into a plurality of time windows, hereinafter, referred to as test time windows. Thereafter, the processor 50 is configured to compare the signal values of the test time windows with a reference signal value of a plurality of reference time windows of one or more reference segments with each of the representations to obtain a difference between the test signal value of each of the test time windows and the reference signal value of the reference time windows of the reference segments. The processor 50 is further configured to define grid points associated with each of the respective test time windows, respective reference time windows and the respective differences. Using the grid points defined, the processor 50 in configured to obtain a warping path over all the test time windows for each of the representations, non-linearly in a predetermined order. The differences associated with the grid points along the warping paths are summed by the processor 50 with respect to each of the representations to obtain a cumulative distance for each of the warping paths. The cumulative distance is the sum of the differences associated with grid points along the warping path and provides a measure of dissimilarity between the reference segments of the representation and the cycle of the test electrophysiological signal. The cumulative distances of the warping paths are analyzed by the processor 50 for classification of the test electrophysiological signal 45. The processor 50 classifies the electrophysiological signal to the morphological class corresponding to the warping path of the representation having the least cumulative distance. According to an embodiment, the processor 50 can be further configured to segment the cycle of the test electrophysiological signal 45 based on the warping path having the least cumulative distance.

A "processor" as used herein is a device for executing machine-readable instructions stored on a computer readable medium, for performing tasks and may comprise any one or combination of hardware and firmware. A processor may also comprise memory storing machine readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

The instructions for performing the functions described herein can be stored at a computer-readable medium providing program code for use to the processor. For the purposes of this description, a computer readable medium can be any apparatus that can comprise, store, communicate, propagate, or transport the program for use by or in connection with the processor. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Figure 2:
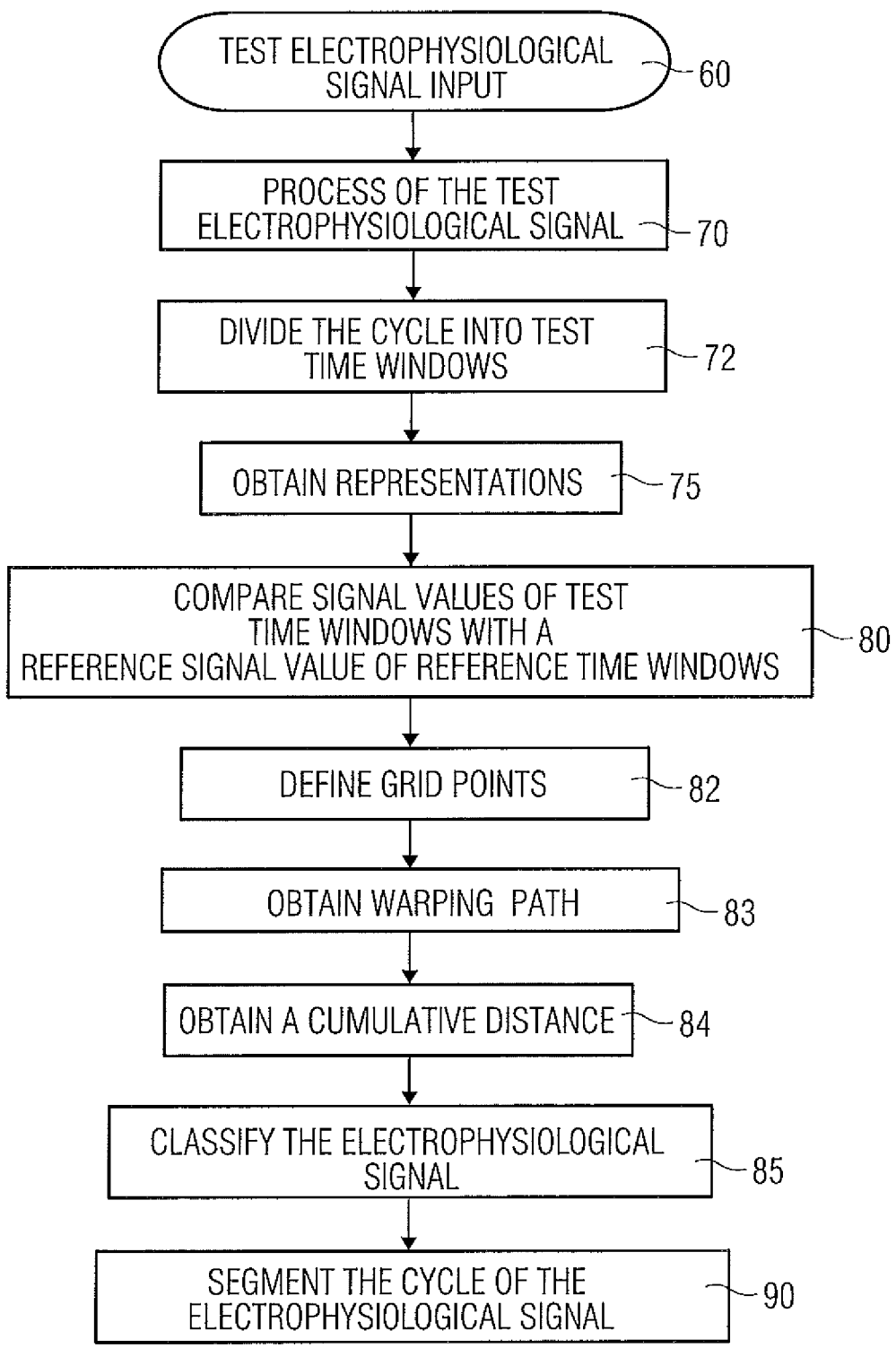
FIG. 2 illustrates a flow chart of a process for analyzing a test electrophysiological signal according to an embodiment herein.

FIG. 2 illustrates a flow chart of a process for analyzing a test electrophysiological signal according to an embodiment herein. The test electrophysiological signal 45 of FIG. 1 can be obtained from the body of the patient using electrophysiological techniques, such as, for example, using electrodes or by optical means. At step 60, the test electrophysiological signal 45 of FIG. 1 representing electrical activity of a bodily part of a patient is acquired by the acquisition device 40 of FIG. 1. At step 70, the acquisition device 35 processes the electrophysiological signal to perform signal preconditioning, and single cycle detection to obtain a single cycle of the test electrophysiological signal 45. As the electrophysiological signals are periodic in nature, one period of the signal is referred herein as a cycle. Next at step 72, the processor 50 divides the cycle of the test electrophysiological signal 45 into a plurality to time windows, hereinafter referred to as test time windows. Moving next to step 75, the processor 50 obtains the representations from the memory device 55. Next, at step 80, the processor 50 compares the signal values of the test time windows with a reference signal value of a plurality of reference time windows of one or more reference segments of each of the representations to obtain a difference between the test signal value of each of the test time windows and the reference signal value of the reference time windows of the reference segments. Moving next to step 82, grid points associated with each of the respective test time windows, respective reference time windows and the respective differences are defined. Next at step 83, a warping path is obtained over all test time windows using the grid points non-linearly in a predetermined order. At step 84, the differences associated with grid points along the warping path are summed to obtain a cumulative distance for each of the warping paths. Next at step 85, the processor 50 identifies the warping path having the least cumulative distance and classifies the electrophysiological signal to the morphological class corresponding to the representation of which the warping path has the least cumulative distance. In an aspect, at step 90, the cycle of the electrophysiological signal 45 is segmented by the processor 50 based on the warping path having the least cumulative distance.

Figure 3:
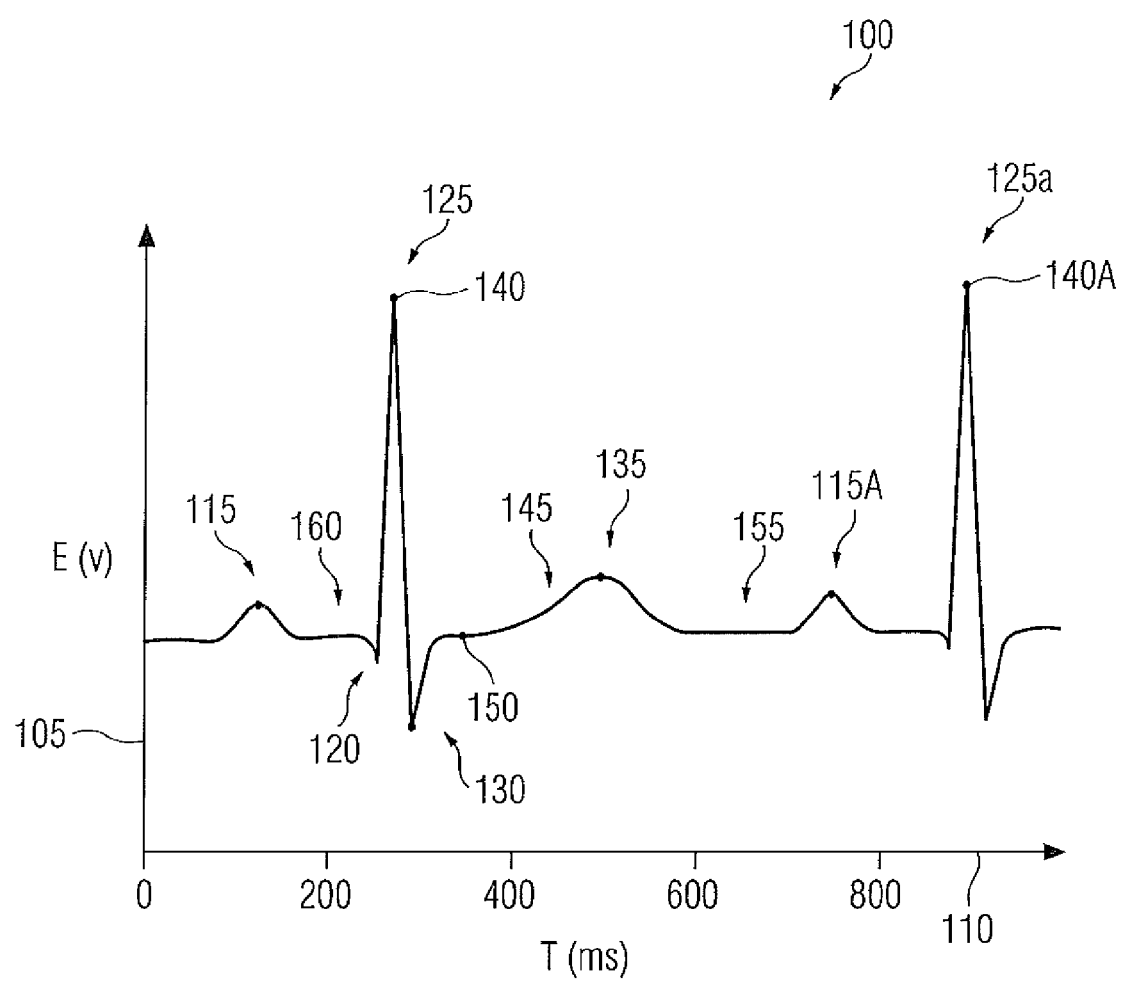
FIG. 3 is a prior art showing an exemplary plot 100 representative of a human Electrocardiogram (ECG) signal as an example of an electrophysiological signal.

FIG. 3 is a prior art, showing an exemplary plot 100 representative of a human Electrocardiogram (ECG) signal as an example of an electrophysiological signal, wherein the axis 105 represents an electrical voltage (V) associated with heart electrical activity of a patient as measured by an ECG electrode and the axis 110 represents time (Ins). From the illustrated example of ECG 100, it can be observed that a single cycle of an ECG signal comprises a plurality of portions. A deflection 115 is known as a "P-wave" and is a resultant of excitation of the atria of the heart. Deflections 120, 125 and 130 are known as "Q-wave," "R-wave," and "S-wave" respectively. The Q-wave, R-wave and S-wave in the ECG waveform result from excitation (de-polarization) of the ventricles of the heart and are hence collectively referred to as a QRS complex. It should be noted that not every QRS complex contains a Q-wave, an R-wave, and an S-wave. By convention, any combination of these waves can be referred to as a QRS complex. Deflection 135 is known as a "T-wave" and is a resultant of recovery (repolarization) of the ventricles. The temporal distance on the ECG waveform from the peak point 140 of a first R-wave 125 to the peak point 140A of a next R-wave 125A is known as an R-R or inter-beat interval. The time duration of the R-R interval referred to as a cardiac cycle or a heart beat cycle.

The portion 145 of ECG 100 between the end of the S-wave 130 and the beginning of T-wave 135 is known as an ST segment. A point 150, referred to as a J-point, marks the end of the QRS complex and is used to indicate the beginning of ST segment 145. The portion 155 of ECG waveform between the end of T-wave 135 of one heart beat cycle and the beginning of P-wave 115A of the successive heart beat cycle is referred to as a TP segment. The portion 160 of ECG waveform between the end of P-wave 115 and the beginning of the QRS segment is referred to as a PQ segment. The TP and PQ segments include generally iso-electric (i.e., flat) portions of the ECG resulting from insignificant heart electrical activity during such time intervals.

Figure 4:
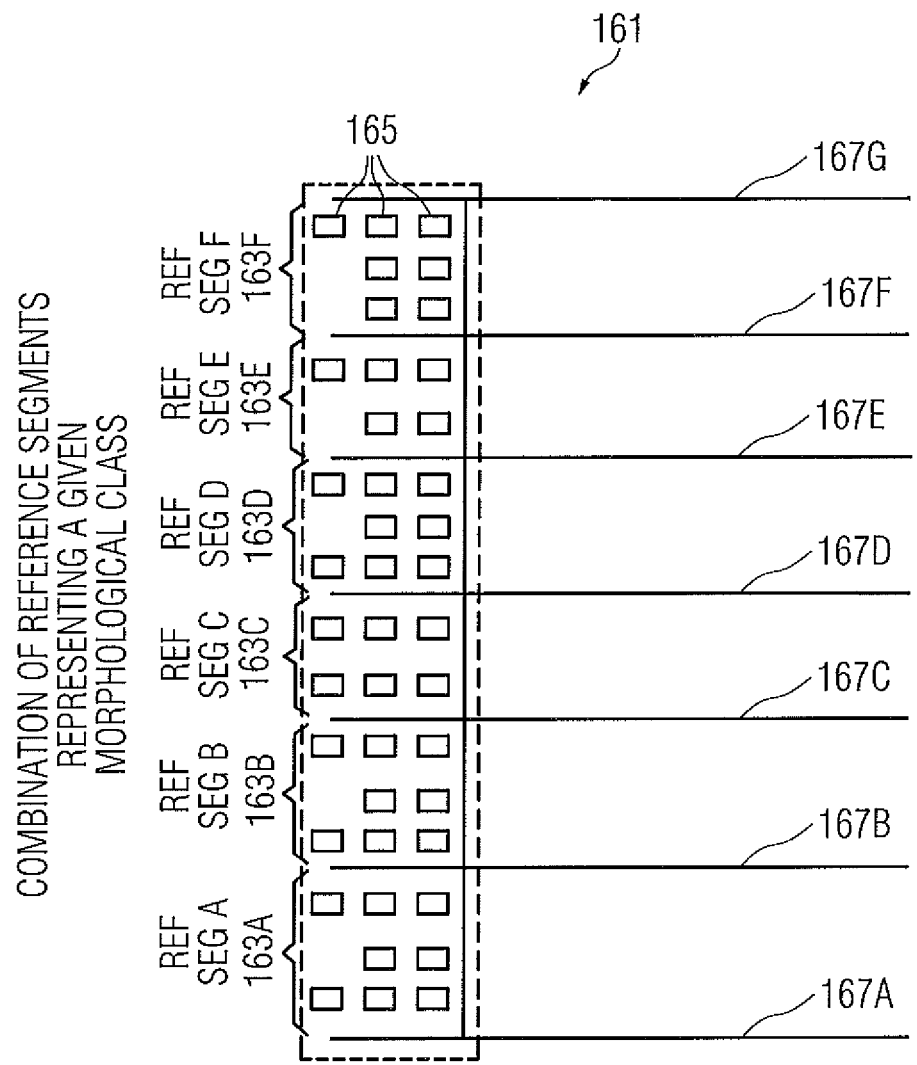
FIG. 4 illustrates an example of a representation representing a morphological class according to an embodiment herein.

FIG. 4 illustrates an example of a representation 161 representing a morphological class according to an embodiment herein. In the shown example of FIG. 4, the representation 161 comprises reference segments referred to as REF SEG A, REF SEG B, REF SEG C, REF SEG D, REF SEG E and REF SEG F designated as 163A, 163B, 163C, 163D, 163E, 163F respectively. The reference segments 163A, 163B, 163C, 163D, 163E, 163F comprise a plurality of reference time windows and each of the reference time windows comprises one or more characteristic vectors 165. The lines designated as 167A, 167B forms the boundary of the reference segment 163A. Similarly, the boundaries of the reference segment 163B are 167B, 167C, of reference segment 163C are 167C, 167D, of reference segment 163D are 167D, 167E, of reference segment 163E are 167E, 167F, and of reference segment 163F are 167F, 167G.

Figure 5:
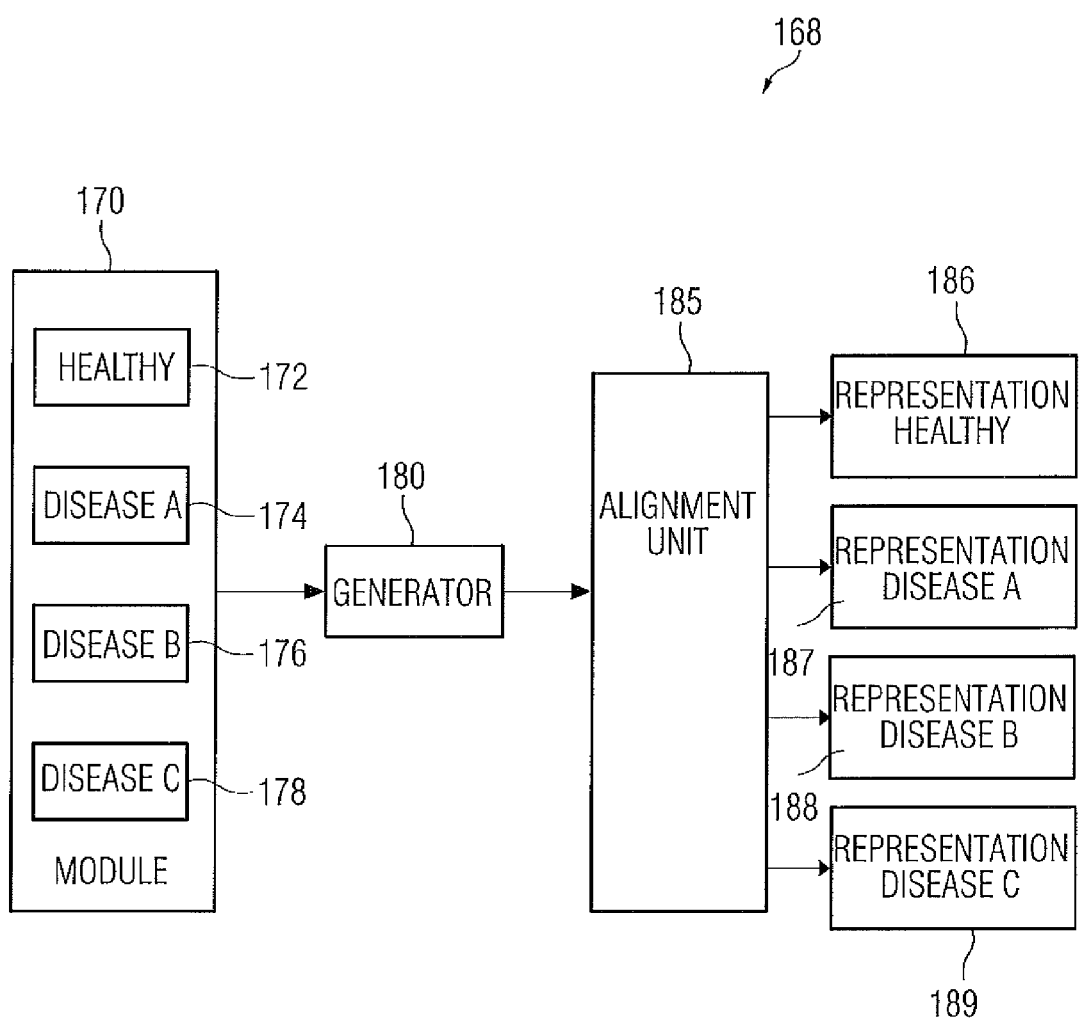
FIG. 5 illustrates a block diagram of a system for generating a representation stored at a memory device according to a first embodiment herein.

FIG. 5 illustrates a block diagram of a system 168 for generating the representations, according to a first embodiment herein. The representations, an example of which has been illustrated in FIG. 4, for each of the morphological classes stored at the memory device 55 can be generated using training data corresponding to each of the respective morphological classes. As mentioned above, the representation corresponding to a morphological class represents training data corresponding to that morphological class. For example, the training data can include one or more portions of electrophysiological signals for each of the morphological classes. The portion of an electrophysiological signal for a morphological class is such that the morphological class can be identified from the characteristics of that portion. In an aspect, the portions can include predetermined training segments of electrophysiological signals. In an aspect, the predetermined training segments can be segments which have been segmented manually, for example by a clinician or a doctor. Accordingly, the module 170 comprises training data corresponding to the morphological classes. In the shown example of FIG. 5, the morphological classes referred to as e, healthy, disease A, disease B, and disease C, designated by the blocks 172, 174, 176, 178 respectively. For example, if the test electrophysiological signal 45 of FIG. 1 is an ECG signal 100 as illustrated in FIG. 3, the morphological classes can be healthy, elevated ST, depressed ST, and arrhythmia and the training data may include one or more predetermined training segments, such as, P wave, PR segment, QRS complex, ST segment, T wave and U wave. The training data corresponding to the morphological classes are provided to a generator 180 for generating one or more reference segments representing each of the one or more similar portions corresponding to each of the morphological classes. The generator 180 can be configured to represent the reference segments using either a state-based statistical model, such as, a hidden Markov model (HMM), or a template based model. The state-based model provides a compact representation of the training data. However, a wide range of intra-class variability may not be captured when the state based model is used. In contrast to this, a template based model is used for representing the training data using the complete information of the training data. This enables capturing the intra-class variability better. Additionally, the template based model provides more accurate boundaries of segmentation of the test electrophysiological signal 45 of FIG. 1.

In an aspect, the generator 180 is configured to generate the reference segments using a template based approach by forming an average time structure for each of the reference segments by averaging signal values of corresponding plurality of similar portions corresponding to a morphological class. The portions can be divided into a sequence of time windows and the signal values of the time windows can be used to form the average time structure. A time window of the portion is a particular time instance of the portion. For example, if the test electrophysiological signal to be analyzed is an ECG 100 of FIG. 3, the similar portions of a morphological class can be a plurality of P waves, a plurality of PR segments, or a plurality of QRS complex, etc. The similar portion of training data for a morphological class can be mapped non-linearly for forming the average time structure. Non-linear mapping can be carried out in accordance with dynamic time warping (DTW) methods or in accordance with Viterbi mapping. The alignment unit 185 aligns the reference segments corresponding to each of the morphological classes to the respective representation. Alignment of the training data at the alignment unit 185 to the respective representations provides the representations for the respective morphological classes, for example, representation healthy 186, representation disease A 187, representation disease B 188, and representation disease C 189.

Figure 6:
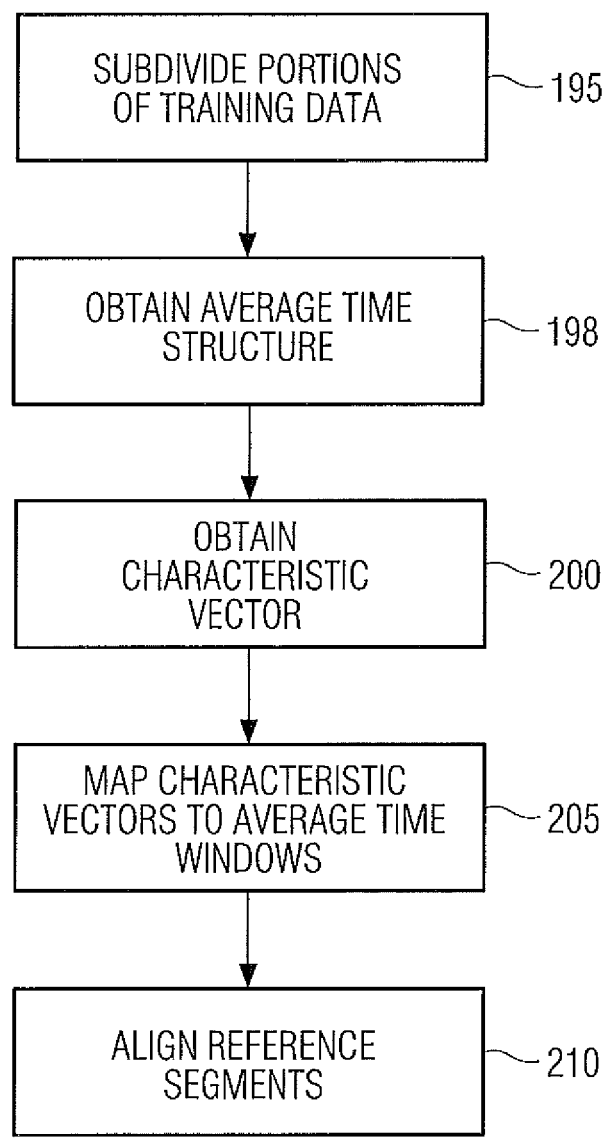
FIG. 6 is a flow diagram illustrating one embodiment of a method of generating a representation using reference segments by averaging corresponding portions of electrophysiological signals.

FIG. 6 is a flow diagram illustrating one embodiment of a method of generating the representations using reference segments by averaging signal values of time windows of corresponding portions of electrophysiological signals. At step 195, each of the portions of the training data is subdivided into a sequence of time windows j. At step 198, the signal values of the corresponding time windows are averaged non-linearly to obtain the average time structure. The average time structure obtained comprises a plurality of average time windows.

Figure 7:
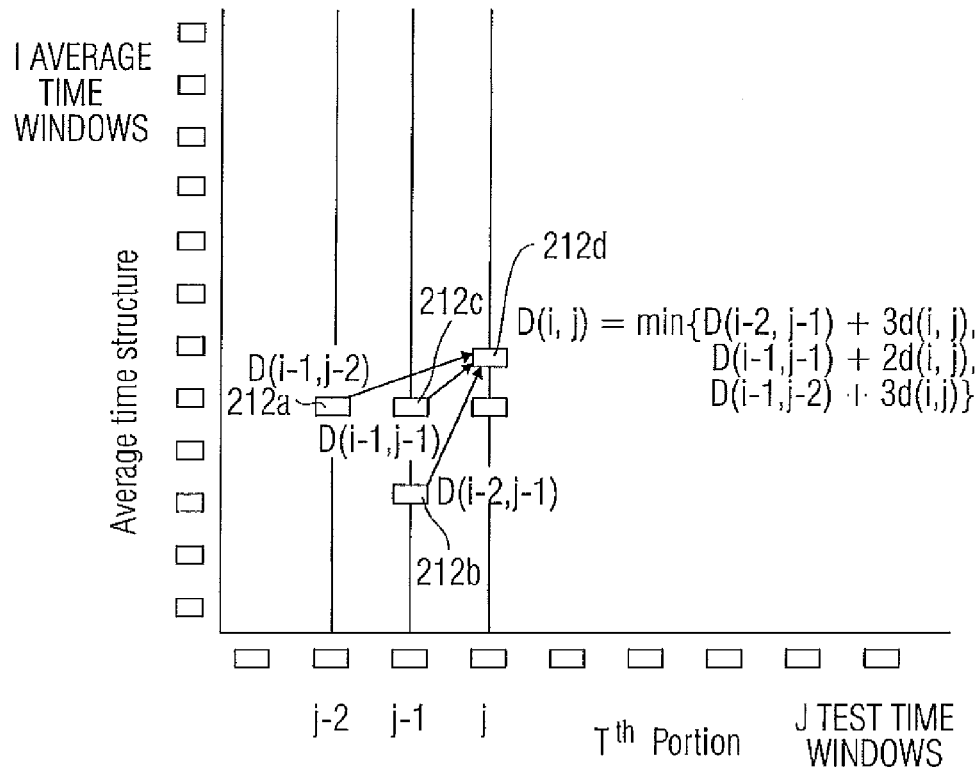
FIG. 7 is a graphical representation of an example of local continuity constraint for computing a distance.

The mapping of the characteristic vectors to obtain the average includes computing a distance D(i, j) between the portions T and the average time structure R. The distance D(i, j) defines a measure of dissimilarity between a portion T and the average time structure R. The computation of the distance D(i, j) includes computation of differences d(i, j) between the signal values of the time window i of the average time structure R and the time window j of the portion T. The difference d(i, j) defines a measure of dissimilarity between the time window i of the average time structure R and the time window j of the portion T. If I is the length of the average time structure R and J is the length of the portion T, the path is forced to begin at point D(1, 1) and end at D(I, J). The distance D(i, j) for DTW can be defined as:

$$\min[D(i-2,j-1)+3d(i,j), D(i-1,j-1)+2d(i,j), D(i-1,j-2)+j)] \quad (1)$$

where, i is the time window index of the average time structure R and j is the time window index of the portion T of the training data. The local continuity constraint for computing the distance D(i, j) is illustrated in the example of FIG. 7. In the shown example of FIG. 7, the local continuity constraint is illustrated as the transition to the grid point 212d can be made only from the grid points 212a, 212b and 212c.

Referring again to FIG. 6, backtracking from the point D(I, J) yields the optimal path p=[$i_k$, $j_k$] and the corresponding mapped set of time windows i of the portion T and average time windows j of the average time structure R [R($i_k$),T($j_k$)], where k, is an index of a grid point on the optimal path p. The average time structure $R_n$ can be computed by successive weighted averaging of n instances as follows:

$$R_n(k) = \left(1 - \frac{1}{n}\right) R_{n-1}(i_k) + \left(\frac{1}{n}\right) T_n(j_k), k = 1 \ldots K \quad (2)$$

where, K is the number of grid points on the optimal path p and $R_{n-1}(i_k)$ is the average of the previous n-1 templates. From equation (2) it can be observed that the averaging of the characteristic vectors is performed successively to obtain the average time structure.

The new time axis for the instance $R_n$ of the average time structure can be computed as:

$$p_1(k) = \left(1 - \frac{1}{n}\right) i_k + \left(\frac{1}{n}\right) j_k, k = 1 \ldots K \quad (3)$$

The time axis obtained using equation (3) is transformed to a constant duration P where P is the constant duration of all instances of the portions. The transformation can be performed as:

$$p_2(k) = \frac{P}{K} p_1(k) \quad (4)$$

Referring now to equation (4), $p_2(k)$ may have non-integer values, and thus, a time axis $p_3(k')$ is defined, where k'=1,2, 3 . . . P. The values of the average time structure $R_n(k)$ are interpolated to get the new average time structure $R_n(k')$.

Additionally, at step 200, in an aspect each portion T of training data is analyzed in each time window i to obtain a characteristic vector for each of the time windows j. A characteristic vector of a time window represents signal value in that time window. At step 205, the characteristic vectors of similar portions T={$T_1, T_2, T_3, \ldots T_n, \ldots$} of a morphological class are mapped non-linearly to the corresponding average time windows of the average time structure R. Thus, in case the characteristic vectors of the similar portions T={$T_1, T_2, T_3, \ldots T_n \ldots$} are mapped to the corresponding average time windows of the average time structure, the average time windows will comprise a plurality of the mapped characteristic vectors. This enables in accounting for the intra-class variability found in the portions of the electrophysiological signals of the training data corresponding to a morphological class.

Figure 8:
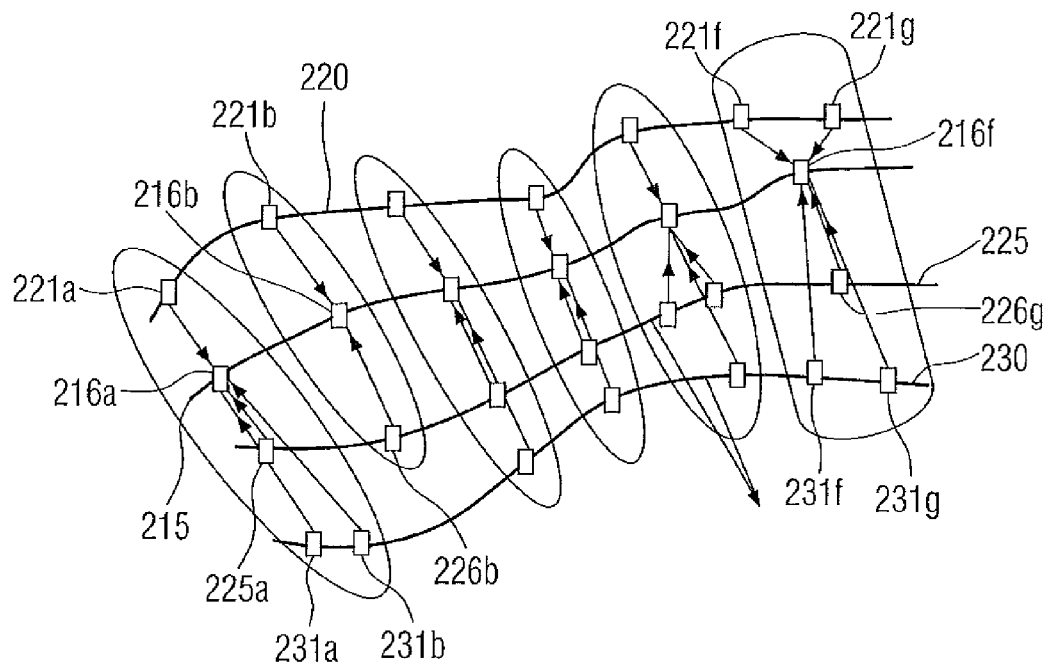
FIG. 8 is an exemplary graphical representation illustrating mapping of characteristic vectors of similar portions of test data with an average time structure.

FIG. 8 is an exemplary graphical representation illustrating mapping of similar portions of training data onto the corresponding average time windows of the average time structure. The average time structure is designated as 215 and the time windows of the average time structure 215 are designated as 216a, 216b, 216e, 216d, 216e and 217f. The similar portions are designated as 220, 225 and 230. As the time windows 221a, 226a, 231a and 231b of the portions 220, 225 and 230 correspond to the time window 216a of the average time structure 215, the characteristic vectors of the time windows 221a, 226a, 231a and 231b are mapped to the average time window 216a of the average time structure 215. Similarly the characteristic vectors of the time windows 221b and 226b are mapped onto the average time window 216b of the average time structure 215.

Referring again to FIG. 6, next at step 210, the reference segments corresponding to a morphological class are aligned by the alignment unit 185 to form the respective representations. The reference segments are aligned by concatenating the reference segments in a predetermined order. For example, for representations according to the embodiments described herein, for ECG 100 of FIG. 3, the reference segments corresponding to P wave, PR segment, QRS complex, ST segment, T wave will be concatenated in the order as they appear in an ECG signal. Reference segments corresponding to U Wave for ECG signals may not be generated as U wave is normally not visible for all ECG signals.

Referring now to FIG. 2, the step 80 of comparing the signal values of each of the test time windows with the reference signal values of the reference time windows of the reference segments, the step 82 of defining of grid points, the step 83 of obtaining the warping path and the step 84 of summing the differences along the grid points of the warping paths will be described in detail now. Typically, as the portions of an electrophysiological signal are in a fixed pattern, the cycle of the test electrophysiological signal is compared with the representations non-linearly in a predetermined order. Non-linear comparison involves expanding or compressing portions of signals so that the portions are aligned for comparison. In contrast, linear comparison involves expanding or compressing the whole signal to align the signals for comparison. As different portions of electrophysiological signals can be of different time scales based on the abnormality of the anatomical part, the non-linear comparison enables in accounting for intra-class variability between the portions in a more appropriate manner. In an aspect, the predetermined order can be the order of the respective portions of an electrophysiological signal. For example, if the electrophysiological signal is an ECG signal, transition into the QRS complex can be done from the PR segment only and transition into the PR segment can be done from the P wave only. In an aspect, the non-linear comparison in the predetermined order can be performed using forced aligned onepass dynamic programming (DP) algorithm.

Figure 9A:
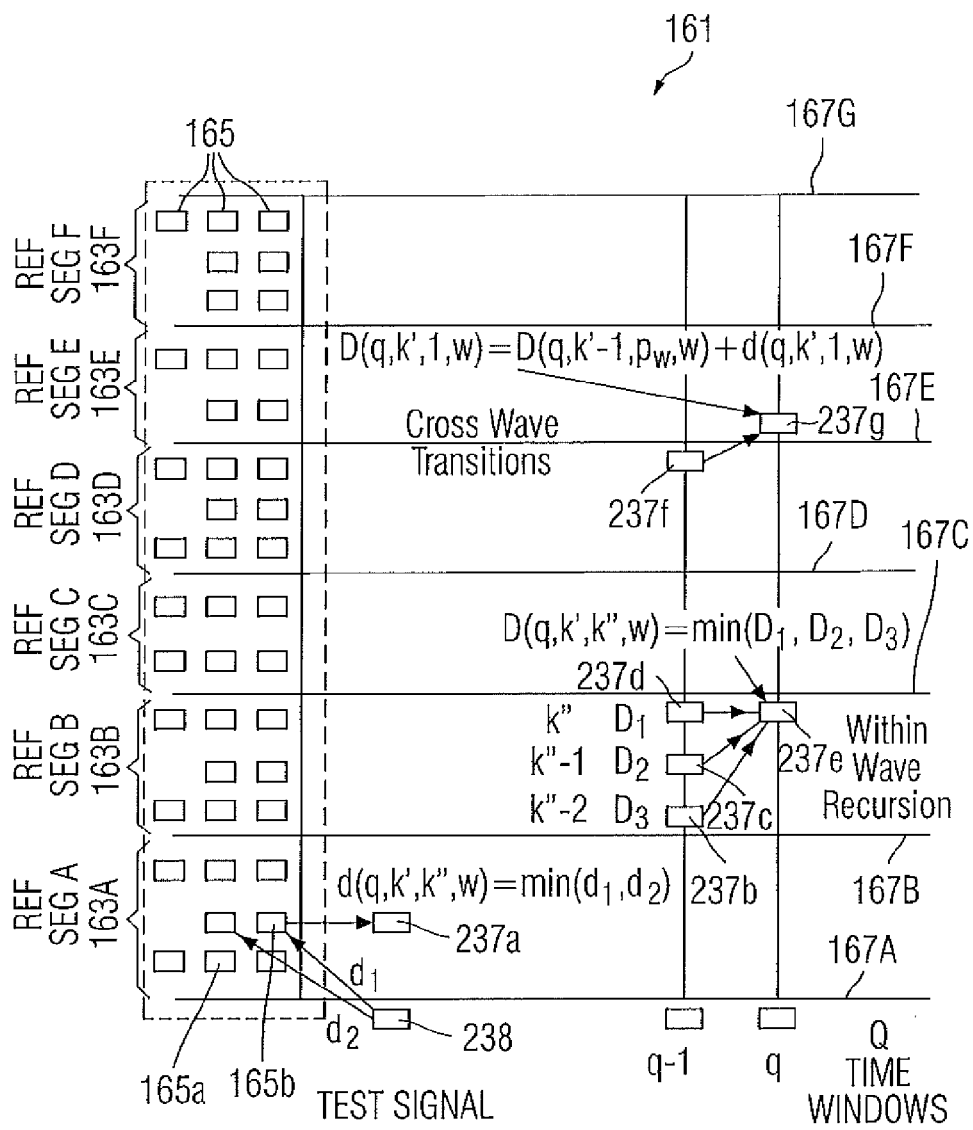
FIG. 9A illustrates a graphical representation of an example of comparison of a representation comprising concatenated reference segments and a cycle of the test electrophysiological signal.

FIG. 9A illustrates a graphical representation of an example of comparison of a the representation 161 comprising concatenated reference segments REF SEG A, REF SEG B, REF SEG C, REF SEG D, REF SEG E and REF SEG F designated as 163A, 163B, 163C, 163D, 163E, 163F respectively and a cycle of the test electrophysiological signal. In the shown example of FIG. 9A, reference segments 163A, 163B, 163C, 163D, 163E, 163F are concatenated in a predetermined order to form the representation 161.

The steps 80, 82, 83, 84 of FIG. 2 will now be described in detail with reference to FIG. 9A. For describing the steps 80, 82, 83, 84 of FIG. 2 mathematically, following assumptions are made. The different morphological classes are denoted as $w=\{w_1, w_2, \ldots w_{N_w}\}$, where w denotes a morphological class, $N_w$ is the total number of morphological classes. Each morphological class corresponds to a representation, such as the representation 161, comprising one or more concatenated reference segments denoted as $R_w(k')$, where $k'=1,2,3 \ldots N_p$, where $N_p$ is the number of reference segments concatenated in the representations corresponding to a morphological class. Each reference segment is denoted as $R'_{k''}$, where $k''=1, 2,3 \ldots P_w$, where $P_w$ is the number of reference time windows in the reference segment. In aspects, where the reference segment comprises an average time structure, each of the average time windows of the average time structure comprises a plurality of corresponding characteristic vectors, such as the characteristic vectors 165, of portions of the training data that are mapped with the respective average time windows of the average time structure. Thus, it is assumed that each time window of the reference segment has M characteristic vectors of the portions of the training data mapped onto it. The test time windows of the cycle of the test electrophysiological signal is denoted as q and Q is the total number of test time windows of the cycle of the test electrophysiological signal. During the comparison process, each of the test signal values of the test time windows q of the cycle are compared with the reference signal values of the reference time windows $P_w$ of the reference segments $R_w(k')$ to obtain a difference. For example, if the characteristic vectors of the similar portions of training data are mapped onto the corresponding average time windows of the average time structure, the difference between test signal values of test time windows of the cycle of the test electrophysiological signal and the corresponding characteristic vectors of reference time windows of the reference segment is computed as the minimum of the differences between the respective test signal values and the respective characteristic vectors of the reference time windows and can be mathematically denoted as:

$$d(q, k', k''w) = \min_{m=1 \ldots M} (d(q, k', k'', w)) \quad (5)$$

where, d (q,k',k"w) is the difference in signal values between the time window q and the $m^{th}$ centroid of the k" time window of the reference segment k' of the morphological class w. Thus computing the difference between the time window of the cycle of the test electrophysiological signal and the characteristic vectors of the potions of the training data aligned with the reference segment enables in combining all possible characteristic vectors of the portions of the training data.

Thereafter, the grid points 237 associated with the respective test time windows, respective reference time windows and the respective differences are defined. In the shown example of FIG. 9A, the test signal value of the test time window 238 is compared with the characteristic vectors 165a and 165b and the difference is computed as the minimum of the two differences. The grid point 237a illustrated is defined by being associated with the difference, and the reference time window containing the characteristic vectors 165a, 165b and the test time window 238. The grid points 237, when tracked, provide the warping path. Thus, the warping path can be obtained from a sequence of grid points 237. The grid points 237 obtained during the comparison can be stored at a memory. The memory can be an internal memory of the processor 50 or an external memory, such as the memory device 55.

As the reference segments are concatenated in a predetermined order in the representation, the warping path can advantageously be obtained using the grid points non-linearly in a predetermined order. Additionally, the warping path can be obtained such that the respective differences between the time windows of the test electrophysiological signal and the corresponding reference time windows of the reference segments are minimized. The differences accumulated between the time window of the test electrophysiological signal and the corresponding time window of the reference segment is denoted as D(q,k',k",w). In an aspect the warping path can be obtained using a forced aligned onepass dynamic programming algorithm. The forced aligned onepass dynamic programming algorithm enables in obtaining the warping path non-linearly in a predetermined order. The forced aligned onepass dynamic programming algorithm will obtain the warping path such that the respective differences over all the test time windows are minimized. In an aspect, the forced aligned onepass dynamic programming algorithm includes using within wave recursion and cross wave recursion to obtain the warping path. The recursions are described in detail in the following paragraphs.

The within wave recursion is computed for all Q time windows of the test electrophysiological signal and all time windows k" of all the reference segments except for k"=1, i.e., the recursion is applied to all time windows except the first time window of the reference segment. The recursion can be computed as:

$$D(q, k', k'', w) = d(q, k', k'', w) + \min_{k''-2 \leq r \leq k''} (D(q-1, k', r, w)) \quad (6)$$

In the shown example of FIG. 9A, the within wave recursion is illustrated as the transition to the grid point 237e from either of the grid points 237b, 237c, 237d. Moreover, it can be observed that the transition is occurring within the same reference segment 163B.

The cross wave recursion is computed for all Q time windows of the test electrophysiological signal and for the time window k"=1 of all the reference segments. This recursion allows a transition into the first time window of a reference segment from the last frame of the previous reference segment. This recursion can be computed as:

$$D(q,k',1,w)=d(q,k',1,w)+D(q,k'-1,P_w,w) \quad (7)$$

For the first reference segment of the representation, i.e., for the reference segment k'=1, the difference is assigned as the difference D(q,k',k",w) accumulated between all the time windows of the test electrophysiological signal and the corresponding time windows of the reference segment. The cross wave recursion is illustrated in the example of FIG. 9A as the transition to the grid point 237g from the grid point 237f. The grid point 237f is associated with the reference segment 163E and the grid point 237g is associated with the reference segment 163F. Thus, the transition from the grid point 237f to the grid point 237g includes the transition from the reference segment 163E to the reference segment 163F.

Figure 9B:
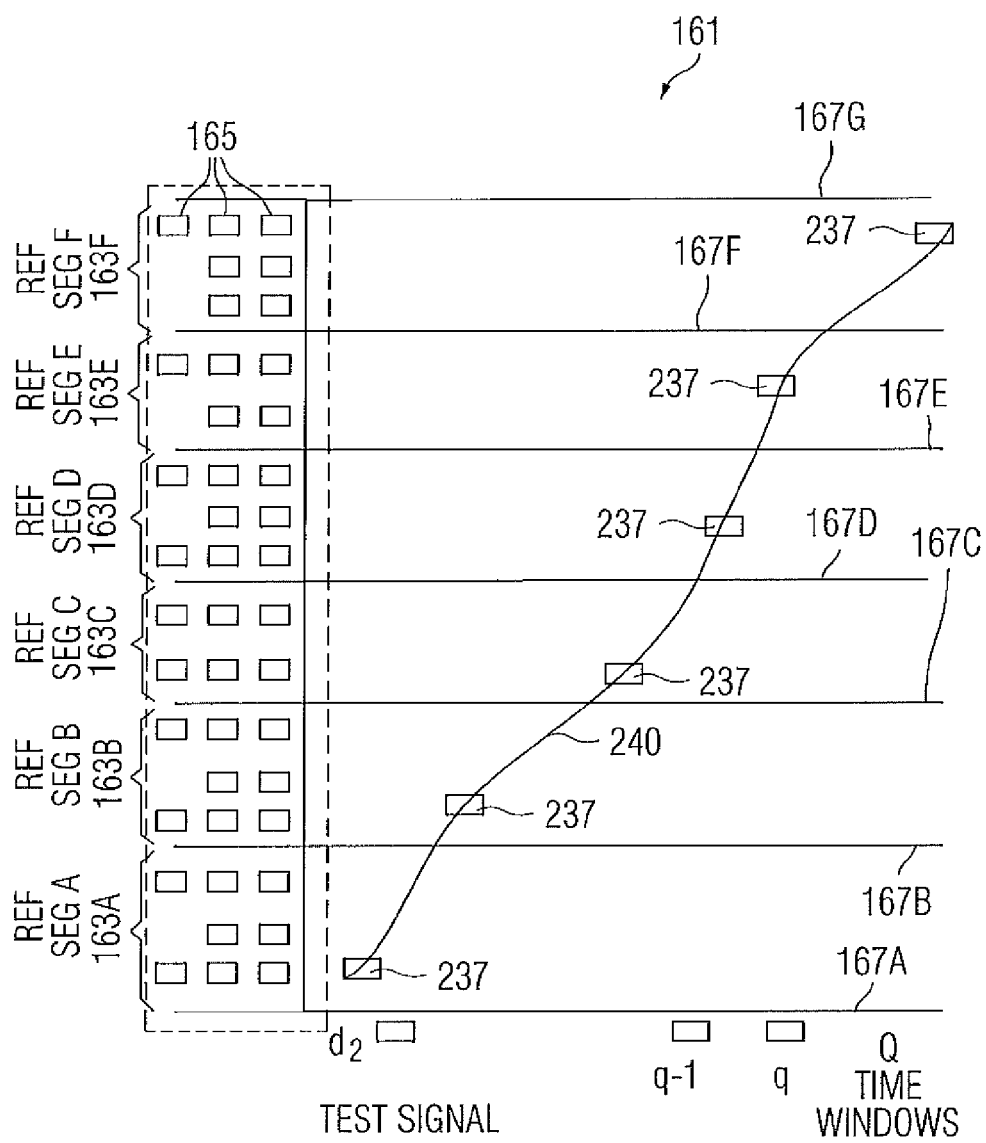
FIG. 9B illustrates an example of a warping path obtained according to the embodiments described herein.

FIG. 9B illustrates an example of a warping path obtained according to the embodiments described herein. In the shown example of FIG. 9B the warping path 240 illustrated is obtained using the grid points 237, such that, the differences along the respective grid points 237 of the warping path 237 is minimum.

Figure 9C:
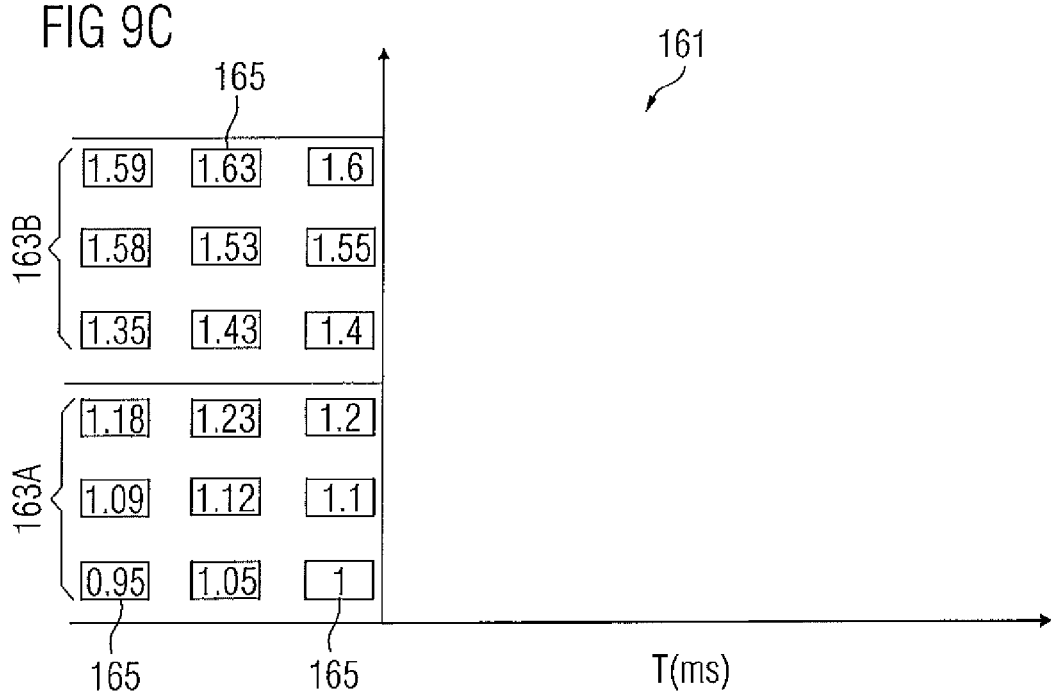
FIGS. 9C and 9D illustrate exemplary representations for obtaining a warping path using real numbers.
Figure 9D:
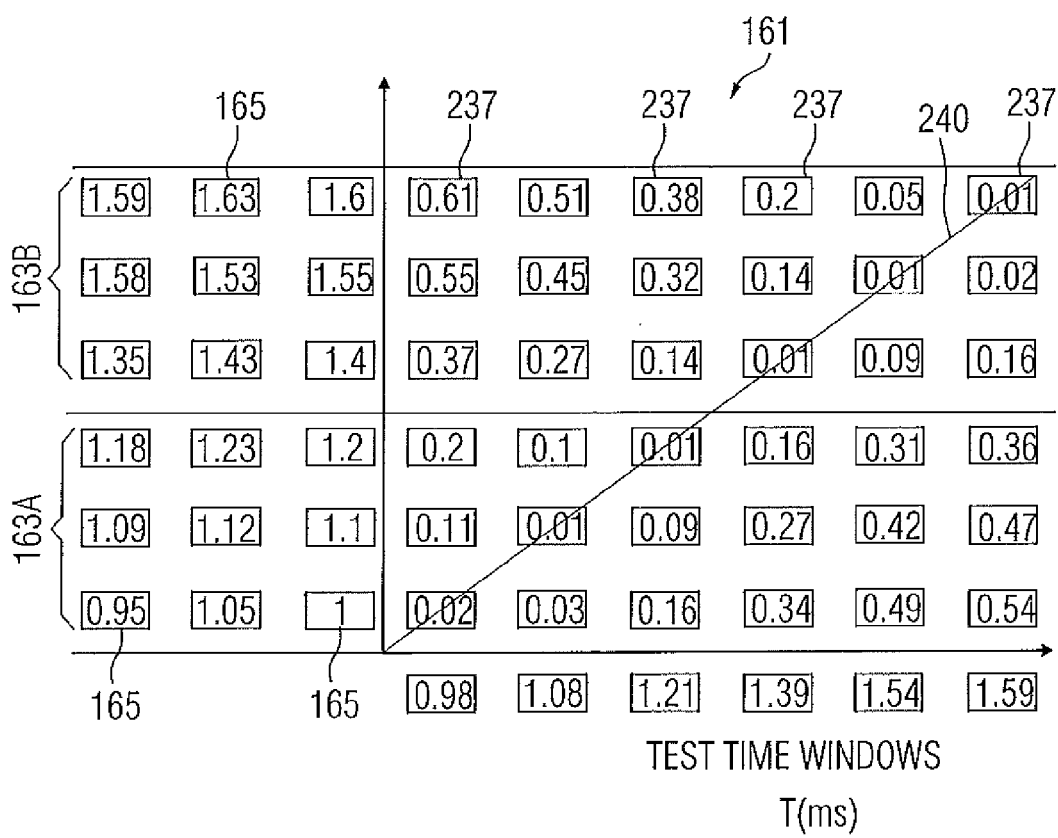

FIGS. 9C and 9D illustrate exemplary representations for obtaining of the warping path using real numbers. Referring now to FIG. 9C, the representation 161 comprises reference segments 163A and 163B. The characteristic vectors 165 of each of the reference time windows depict the corresponding signal values. Referring now to FIG. 9D, the signals values of the test time windows of the cycle of the test electrophysiological signal are compared with the values of the characteristic vectors 165 of the of the reference segments 163A and 163B. The difference is selected as the minimum of the differences between the test signal value and the values of the characteristic vectors 165 of a reference time window. The grid points 237 are defined in association with the differences, respective reference time windows and the respective test time windows. The warping path 240 is obtained using the grid points 237 such that the sum of the differences along the grid points 237 of the warping path 240 is minimized.

Referring now again to FIG. 9A, at the end of the recursion process with respect to Q time windows of the test electrophysiological signal, the cumulative distance $D_w$ computed by the processor 50 of FIG. 1 for the warping path of the test electrophysiological signal can be denoted as:

$$D_w = D(Q, N_p, P_w, w) \quad (8)$$

Referring now to step 85 of FIG. 2, the warping path having the least cumulative distance is determined. The least cumulative distance D* can be determined using the following condition:

$$D^* = \min_{1 \le w \le N_W} D_w \quad (9)$$

Figure 10:
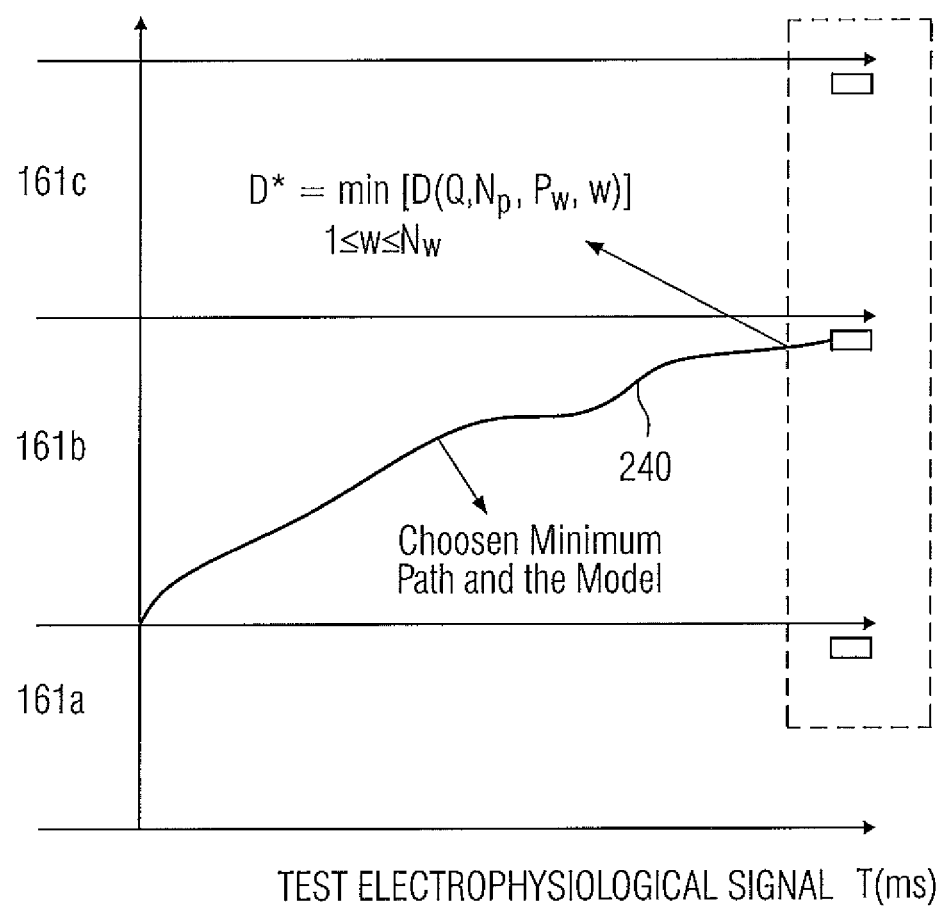
FIG. 10 illustrates an exemplary graphical representation of classification of the test electrophysiological signal to the morphological class for which a warping path has the least cumulative distance.

The morphological class for the representation for which the warping path has the least cumulative distance is identified as the class of the test electrophysiological signal 45. FIG. 10 illustrates an exemplary graphical representation of classification of the test electrophysiological signal to the morphological class for which the warping path 240 has the least cumulative distance. In the shown example of FIG. 10, three representations 161a, 161b and 161c are illustrated for explanation purposes. It is shown that the warping path 240 of the representation 161b has the least cumulative distance amongst the warping paths of the representations 161a, 161b and 161c. Thus, the test electrophysiological signal 45 of FIG. 1 can be classified to morphological class corresponding to the representation 161b.

Figure 11:
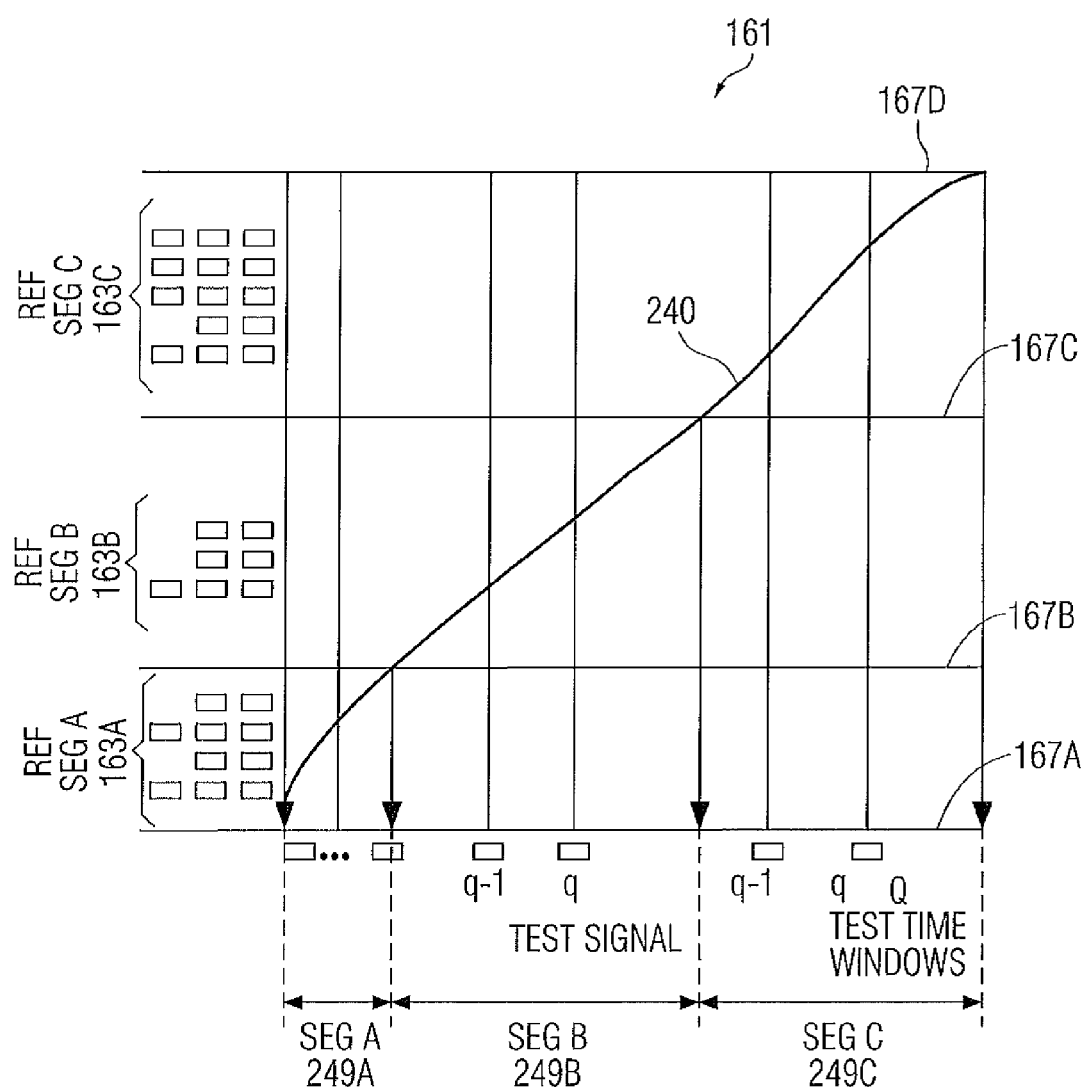
FIG. 11 illustrates an exemplary graphical representation of segmentation of the test electrophysiological signal.

Referring now to step 90 of FIG. 2, the segments of the cycle of the test electrophysiological signal 45 can be obtained using the warping path having the least cumulative distance. The segments of the test electrophysiological signal are obtained as the respective time periods of the intersection of the warping path 240 with the respective boundaries of the reference segments of the representation. FIG. 11 illustrates an exemplary graphical representation of segmentation of the test electrophysiological signal. In the shown example of FIG. 11, the representation 161 comprises three reference segments REF SEG A 163A, REF SEG B 163B, REF SEG 3 163C, concatenated in a predetermined order. The warping path of the cycle of the test electrophysiological signal 45 of FIG. 1 is designated as 240. The boundaries of the reference segment 163A are 167A, 167B. The boundaries of the reference segment 163B are 167B, 167C. The boundaries of the reference segment 163C are 167C, 167D. The corresponding segments SEG A 249A, SEG B 249B, SEG C 249C of the cycle of the test electrophysiological signal 45 are determined as the time periods of the intersection of the warping path 240 with the corresponding boundaries 167A, 167B, 167C, 167D of the reference segments 163A, 163B, 163C. As illustrated in the example of FIG. 11, the segment 249A of the cycle of test electrophysiological signal 45 can be determined as the time period of the intersection of the warping path 240 with the boundaries 167A, 167B of the reference segment 163A. Similarly, the segments 249B, 249C of the cycle of the test electrophysiological signal 45 can be determined as the time period of the intersection of the warping path 240 with the boundaries 167B, 167C of 163B and 167C, 167D of 163C respectively.

FIG. 12 illustrates a flow chart of a process used by system 10 for analyzing an electrophysiological signal according to an embodiment herein. The electrophysiological signal can be obtained from the body of the patient using electrophysiological techniques, such as, for example, using electrodes or by optical means. Following the start step at 250, at step 255, the electrophysiological signal representing electrical activity of a bodily part of a patient is acquired by the acquisition device 40. At step 260, a cycle of the test electrophysiological signal 45 is divided into a plurality of test time windows. Next at step 265, a test signal value of each of the plurality of test time windows is compared with a reference signal value of a plurality of reference time windows of one or more reference segments of a plurality of respective representations representing a plurality of respective predetermined morphological classes to obtain a difference between the test signal value of each of the plurality of test time windows and the reference signal value of the plurality of reference time windows of the one or more reference segments. Moving next to step 267, a plurality of grid points are defined associated with the respective test time windows, respective reference time windows and the respective differences. Next at step 270, a warping path is obtained over all test time windows using the grid points non-linearly in a predetermined order. At step 275, differences along the grid points of each of the warping paths corresponding to each of said plurality of respective representations are summed to obtain a cumulative distance for each of said warping paths. Next at step 280, the test electrophysiological signal 45 of FIG. 1 is classified into one of the predetermined morphological classes corresponding to the warping path having the least cumulative distance. The process of FIG. 12 terminates at step 285.

Figure 13A:
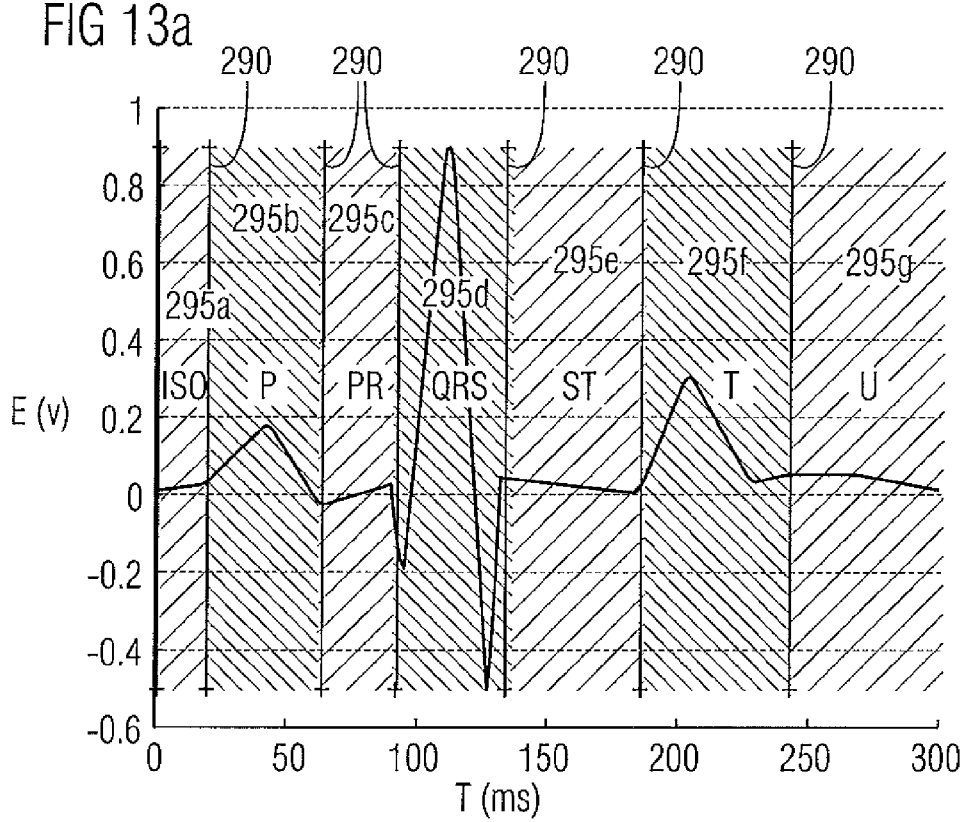
FIG. 13a through FIG. 13e provides graphical representation of experiment results of classification and segmentation for ECG signals with respect to different morphological classes obtained using the embodiments described herein.
Figure 13B:
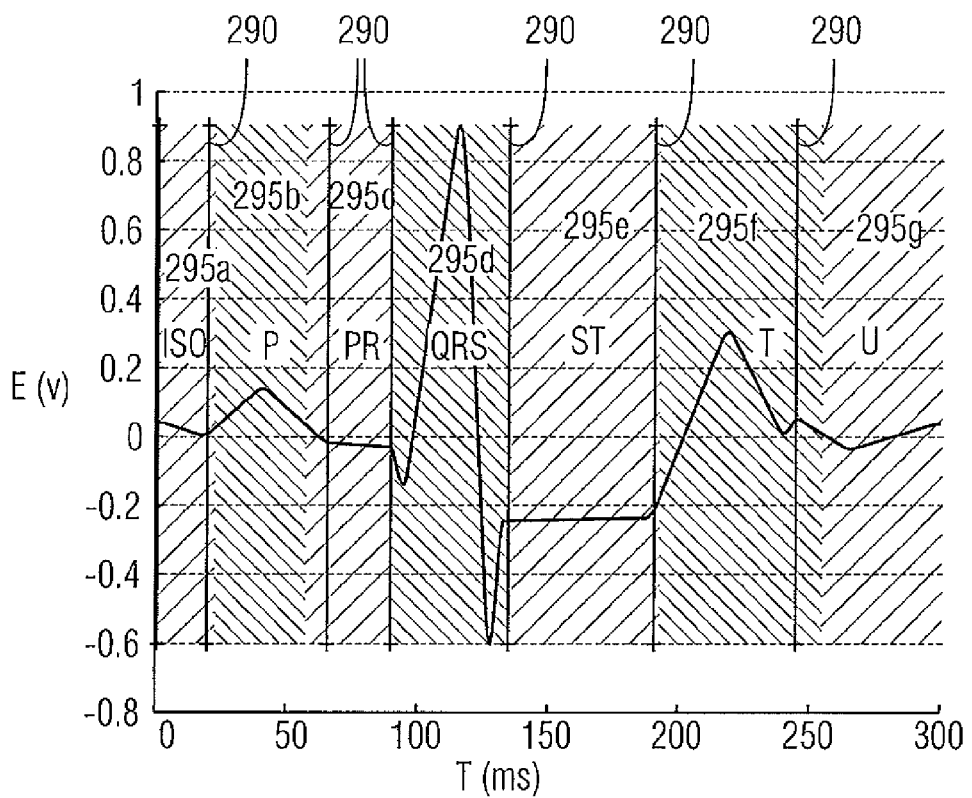
Figure 13C:
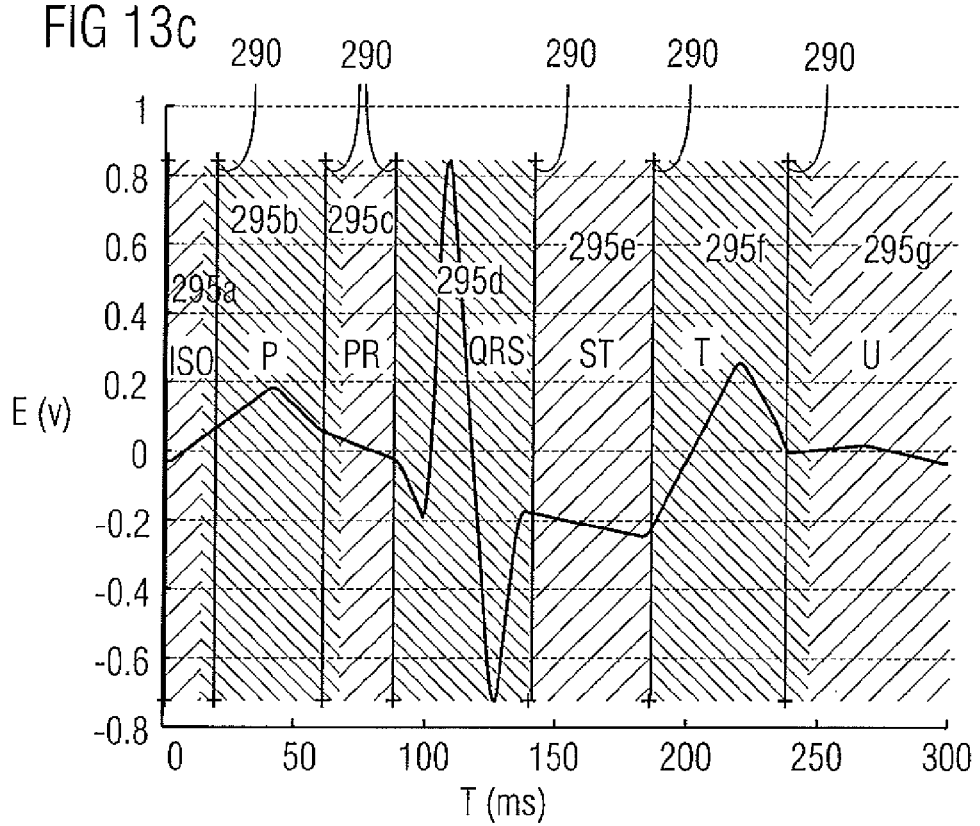
Figure 13D:
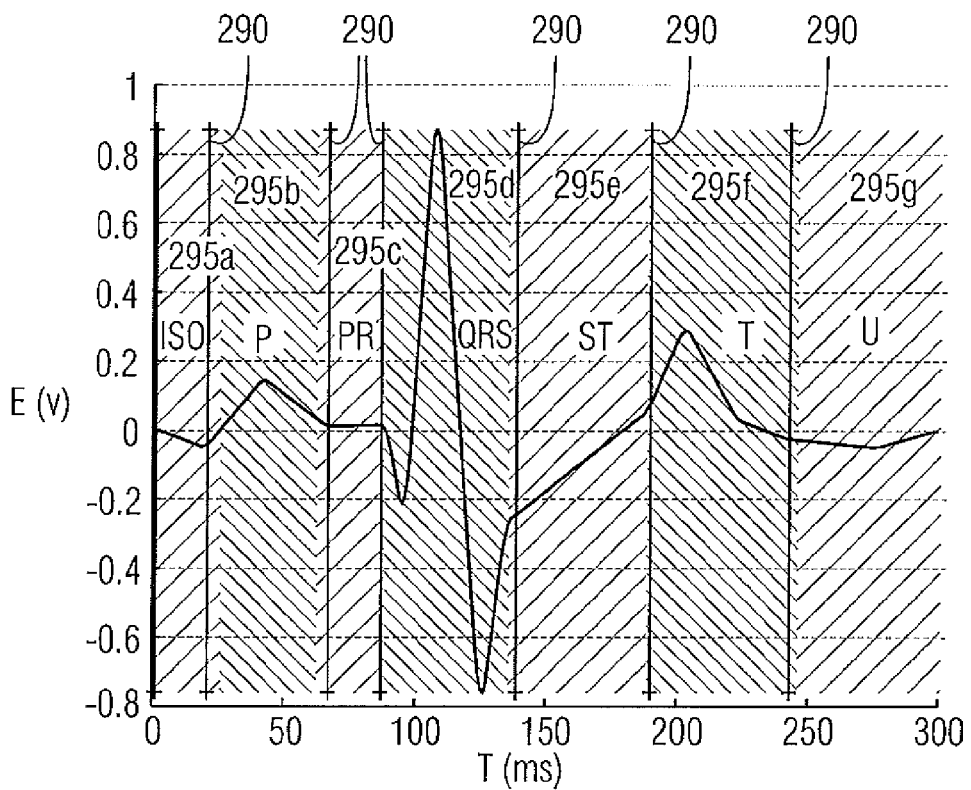
Figure 13E:
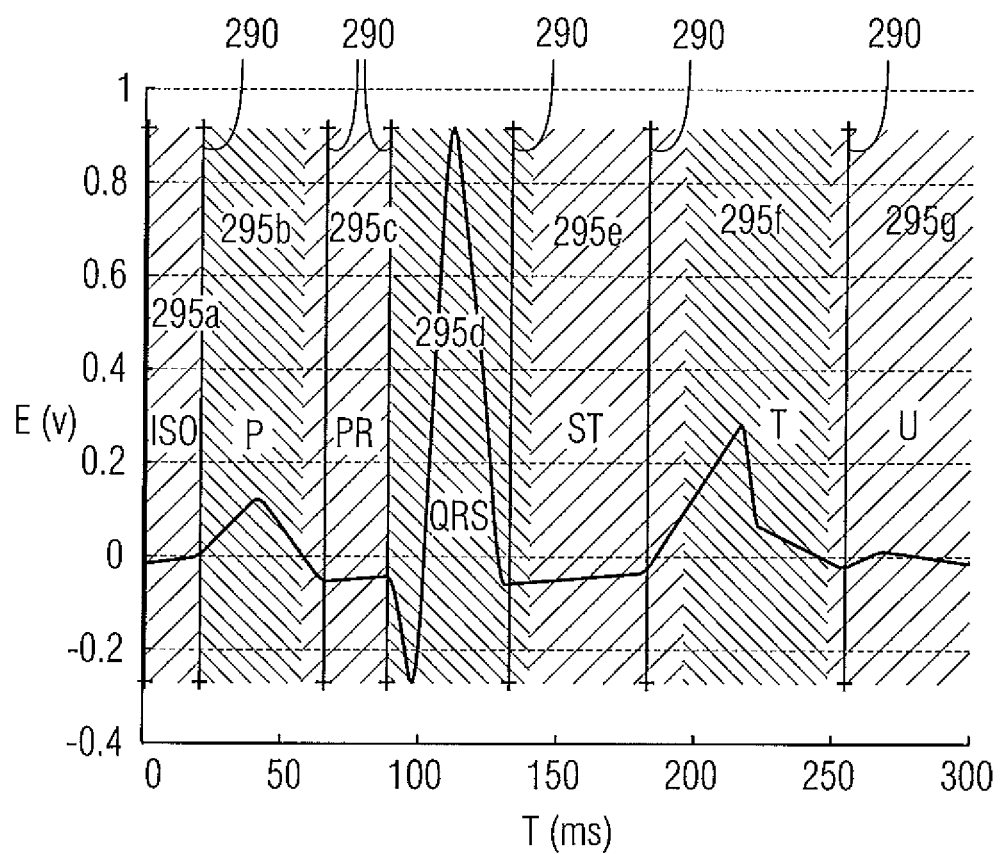

FIG. 13a through FIG. 13e provide a graphical representation of experiment results of classification and segmentation for ECG signals with respect to different morphological classes obtained using the embodiments described herein. For the experiment purpose, the ECG data was generated using the ECG function in MALTAB. The morphological classes for the ECG consider herein are, normal ST segment, horizontal depressed ST segment, downsloping depressed ST segment, upsloping depressed ST segment, and elevated ST segment. The training data comprised of fifty similar portions for each of the morphological class. Ten test ECG signals were generated for each of the morphological classes. FIG. 13a provides the graphical representation of segmentation of an ECG signal with normal ST segment. FIG. 13b provides the graphical representation of segmentation of an ECG signal with horizontal depressed ST segment. FIG. 13c provides the graphical representation of segmentation of an ECG signal with downsloping depressed ST segment. FIG. 13d provides the graphical representation of segmentation of an ECG signal with upsloping depressed ST segment. FIG. 13e provides the graphical representation of classification and segmentation of an ECG signal with elevated ST segment. In the shown FIGS. 13a to 13e, the corresponding real segments of the ECG signal are within the boundaries designated by the lines 290. The segmentation obtained using the embodiments described herein is illustrated by the corresponding hatched sections. In the shown examples of FIGS. 13a to 13e, two different hatching patterns have been used to distinguish between two adjacent segments. The hatched portion 295a designates a part of the iso-electric line. The hatched portions 295b, 295c, 295d, 295e, 295f and 295g designate P wave, PR segment, QRS complex, ST segment, T wave and U wave respectively.

The embodiments described herein enable in more accurate automated classification and segmentation of electro-physiological signals. Generation of the reference segments using non-parametric techniques enables in taking account of intra-class variability of the training data. Additionally, the segmentation obtained using the embodiments herein are more accurate as the temporal continuity of the reference segments of the representations are maintained during the formation of the representations. Mapping multiple characteristic vectors with the respective time windows of the average time structure to form the representations reduces the amount of processing required and thus, reduces the computational complexity for forming the representations.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A system for analyzing an electrophysiological signal, comprising:
   an acquisition device for acquiring a test electrophysiological signal associated with an anatomical part of a patient; and
   a processor configured to:
   divide a cycle of said test electrophysiological signal into a plurality of test time windows;
   compare a test signal value of each of said plurality of test time windows with a reference signal value of a plurality of reference time windows of one or more reference segments of a plurality of respective representations representing a plurality of respective predetermined morphological classes to obtain a difference between said test signal value of each of said plurality of test time windows and said reference signal value of said plurality of reference time windows of said one or more reference segments, said one or more reference segments being formed using respective training data;
   define a plurality of grid points associated with respective ones of said test time windows, respective reference time windows and respective differences;
   obtain a warping path over said test time windows using said grid points non-linearly in a predetermined order;
   sum differences along said grid points of each of said warping paths corresponding to each of said plurality of respective representations to obtain a cumulative distance for each of said warping paths; and
   classify said test electrophysiological signal into one of said respective predetermined morphological classes corresponding to said warping path of said respective representation having the least said cumulative distance.

2. The system according to claim 1, wherein the training data comprises one or more predetermined training segments corresponding to each of said respective predetermined morphological classes.

3. The system according to claim 2, wherein each of said reference segments for each of said plurality of respective representations comprises an average time structure, said average time structure formed by averaging signal values of corresponding time windows of a plurality of said predetermined training segments non-linearly, said average time structure having a plurality of average time windows, said average time windows being said reference time windows of said reference segments.

4. The system according to claim 3, wherein said average time windows comprises
   a characteristic vector of each of said time windows of the plurality of said predetermined training segments mapped onto the corresponding said average time windows such that said average time windows comprise a plurality of characteristic vectors, said characteristic vectors mapped non-linearly, said characteristic vector for each of said time windows obtained by analyzing the respective said time window.

5. The system according to claim 4, wherein the processor is configured to determine said difference as the minimum of the differences between said test time window and said characteristic vectors of said reference time windows.

6. The system according to claim 1, wherein said respective representation comprises a plurality of said reference segments concatenated in a predefined order.

7. The system according to claim 1, wherein the processor is configured to obtain said warping path using a forced aligned onepass dynamic programming algorithm.

8. The system according to claim 1, wherein the processor is further configured to segment said cycle into one or more segments based on said warping path of said cycle of electrophysiological signal corresponding to said respective representation having the least said cumulative distance.

9. The system according to claim 8, wherein said one or more segments of said cycle are derived as respective time periods of intersection of said warping path with boundaries of respective said one or more reference segments of said respective training model having the least said cumulative distance.

10. The system according to claim 1, wherein said test electrophysiological signal is a electrocardiogram (ECG) signal representing heart beat cycles of a heart of said patient, said one or more predetermined respective training segments corresponding to said plurality of respective predetermined morphological classes include, one or more of a respective P-wave segment, one or more of a respective PR segment, one or more of a respective QRS complex segment, one or more of a respective ST segment, and one or more of a respective T-wave segment.

11. A system for analyzing an electrophysiological signal, comprising:
an acquisition device for acquiring a test electrophysiological signal associated with an anatomical part of a patient;
a memory device having stored therein a plurality of respective representations representing a plurality of respective predetermined morphological classes, each of said plurality of respective representations formed using one or more reference segments, each of said one or more reference segments being formed using respective training data, each of said reference segments comprising a plurality of reference time windows; and
a processor configured to:
divide a cycle of said test electrophysiological signal into a plurality of test time windows;
compare a test signal value of each of said plurality of test time windows with a reference signal value of said plurality of reference time windows of said one or more reference segments to obtain a difference between the test signal value of each of said plurality of test time windows and said reference signal value of said plurality of reference time windows of said one or more reference segments,
define a plurality of grid points associated with the respective ones of said test time windows, respective reference time windows and respective differences;
obtain a warping path over said test time windows using said grid points non-linearly in a predetermined order;
sum differences along said grid points of each of said warping paths corresponding to each of said plurality of respective representations to obtain a cumulative distance for each of said warping paths; and
classify said test electrophysiological signal into one of said respective predetermined morphological classes corresponding to said warping path of said respective representation having the least said cumulative distance.

12. A method of analyzing an electrophysiological signal, comprising:
acquiring a test electrophysiological signal associated with an anatomical part of a patient;
dividing a cycle of said test electrophysiological signal into a plurality of test time windows by a processor;
comparing, by said processor, a test signal value of each of said plurality of test time windows with a reference signal value of a plurality of reference time windows of one or more reference segments of a plurality of respective representations representing a plurality of respective predetermined morphological classes to obtain a difference between said test signal value of each of said plurality of test time windows and said reference signal value of said one or more reference segments, said one or more reference segments being formed using respective training data;
defining a plurality of grid points associated with the respective ones of said test time windows, respective reference time windows and respective differences, by said processor;
obtaining a warping path over said test time windows using said grid points non-linearly in a predetermined order by said processor;
summing differences along said grid points of each of said warping paths corresponding to each of said plurality of respective representations to obtain a cumulative distance for each of said warping paths by said processor; and
classifying said test electrophysiological signal into one of said respective predetermined morphological classes corresponding to said warping path of said respective training model having the least said cumulative distance by said processor.

13. The method according to claim 12, wherein said training data comprises one or more predetermined training segments corresponding to each of said respective predetermined morphological classes.

14. The method according to claim 13, wherein each of said reference segment for each of said plurality of respective representations comprises an average time structure, said average time structure formed by averaging signal values of corresponding said time windows of a plurality of said predetermined training segments non-linearly, said average time structure having a plurality of average time windows, said average time windows being the reference time windows of said reference segments.

15. The method according to claim 14, wherein said average time windows comprises
a characteristic vector of each of said time windows of the plurality of said predetermined training segments mapped onto the corresponding said average time windows such that said average time windows comprise a plurality of characteristic vectors, said characteristic vectors mapped non-linearly, said characteristic vector for each of said time windows obtained by analyzing the respective said time window.

16. The method according to claim 15, wherein said difference is determined by said processor as the minimum of the differences between said test time window and said characteristic vectors of said reference time windows.

17. The method according to claim 16, wherein said respective representation comprises a plurality of said reference segments concatenated in a predefined order.

18. The method according to claim 12, wherein said warping path is obtained by said processor using a forced aligned onepass dynamic programming algorithm.

19. The method according to claim 12, further comprising segmenting by said processor said cycle into one or more segments based on said warping path of said cycle corresponding to said respective representation having the least said cumulative distance.

20. The method according to claim 18, wherein said one or more segments of said cycle are derived as respective time periods of intersection of said warping path with boundaries of respective said one or more reference segments of said respective representation having the least said cumulative distance.

* * * * *